US010357503B2

(12) United States Patent
Wald et al.

(10) Patent No.: US 10,357,503 B2
(45) Date of Patent: *Jul. 23, 2019

(54) FORMULATION FOR THE PREVENTION OF CARDIOVASCULAR DISEASE

(71) Applicants: Nicholas J Wald, Oxford (GB); Malcolm R Law, London (GB)

(72) Inventors: Nicholas J Wald, Oxford (GB); Malcolm R Law, London (GB)

(*) Notice: Subject to any disclaimer, the term of this patent is extended or adjusted under 35 U.S.C. 154(b) by 1133 days.

This patent is subject to a terminal disclaimer.

(21) Appl. No.: 13/799,682

(22) Filed: Mar. 13, 2013

(65) Prior Publication Data
US 2013/0210778 A1 Aug. 15, 2013

Related U.S. Application Data

(63) Continuation of application No. 10/257,429, filed as application No. PCT/GB01/01618 on Apr. 10, 2001, now Pat. No. 8,470,868.

(30) Foreign Application Priority Data

Apr. 10, 2000 (GB) .................................. 0008791.6
Jan. 9, 2001 (GB) .................................. 0100548.7

(51) Int. Cl.
A01N 43/38 (2006.01)
A61K 31/60 (2006.01)
A61K 31/165 (2006.01)
A61K 31/366 (2006.01)
A61K 31/40 (2006.01)
A61K 31/401 (2006.01)
A61K 31/519 (2006.01)
A61K 31/54 (2006.01)
A61K 31/549 (2006.01)
A61K 31/616 (2006.01)
A61K 38/55 (2006.01)
A61K 45/06 (2006.01)
A61K 31/351 (2006.01)
A61K 31/402 (2006.01)

(52) U.S. Cl.
CPC ............ *A61K 31/60* (2013.01); *A61K 31/165* (2013.01); *A61K 31/351* (2013.01); *A61K 31/366* (2013.01); *A61K 31/40* (2013.01); *A61K 31/401* (2013.01); *A61K 31/402* (2013.01); *A61K 31/519* (2013.01); *A61K 31/54* (2013.01); *A61K 31/549* (2013.01); *A61K 31/616* (2013.01); *A61K 38/55* (2013.01); *A61K 45/06* (2013.01)

(58) Field of Classification Search
USPC ....................................................... 514/412
See application file for complete search history.

(56) References Cited

U.S. PATENT DOCUMENTS

| 3,657,316 | A |   | 4/1972  | Samuelsson et al. |
|-----------|---|---|---------|-------------------|
| 4,677,102 | A | * | 6/1987  | Baldwin et al. ............. 514/218 |
| 4,794,111 | A |   | 12/1988 | Posanski et al. |
| 4,808,413 | A | * | 2/1989  | Joshi et al. .................. 424/458 |
| 4,842,859 | A |   | 6/1989  | Liu |
| 5,385,937 | A |   | 1/1995  | Stamler et al. |
| 5,663,186 | A | * | 9/1997  | Nelson et al. ................ 514/381 |
| 5,686,451 | A |   | 11/1997 | Kristianson et al. |
| 5,948,443 | A |   | 9/1999  | Riley et al. |
| 5,962,020 | A | * | 10/1999 | DeFelice ...................... 424/464 |
| 6,054,128 | A |   | 4/2000  | Wakat |
| 6,162,802 | A |   | 12/2000 | Papa et al. |
| 6,673,831 | B1| * | 1/2004  | Tobert ...................... 514/252.17 |
| 2003/0175344 | A1 |  | 9/2003 | Wald et al. |

FOREIGN PATENT DOCUMENTS

| EP | 0948265 | 4/2003 |
|----|---------|--------|
| EP | 0930831 | 7/2003 |
| WO | WO 97/38694 | 10/1997 |
| WO | WO 98/19690 | 5/1998 |
| WO | WO 98/23494 | 6/1998 |
| WO | WO 98/28989 | 7/1998 |
| WO | WO 98/33494 | 8/1998 |
| WO | WO 99/07400 | 2/1999 |
| WO | WO 99/11260 | 3/1999 |
| WO | WO 9920110 A1 * | 4/1999 |
| WO | WO 01/15674 | 3/2001 |

OTHER PUBLICATIONS

MacMahon et al. (A pilot study with simvastatin and folic acid/vitamin B12 in preparation for the Study of the Effectiveness of Additional Reductions in Cholesterol and Homocysteine (SEARCH). Nutrition, metabolism, and cardiovascular diseases: NMCD 10.4 (2000): 195-203).*

Feldman et al., "Why, What and How to Implement Reduction of Cardiovascular Risk Factors by Diet", Journal of the American College of Nutrition, 1987, 6(6), 475-483.

Forbes et al., "Chemical Abstract No. 131:153567", Thromb. Haemostasis, 1999, 25(suppl. 2), 55-59.

Law et al., "Environmental Tobacco Smoke Exposure and Ischaemic Heart Disease: An Evaluation of the Evidence", BMJ, Oct. 1997, 315, 973-988.

Law et al., "Quantifying Effect of Stains on low density lipoprotein cholesterol, ischaemic heart disease, and stroke: Systematic review and meta-analysis", BMJ, Jun. 2003, 326, 7 pages.

(Continued)

Primary Examiner — Layla Soroush
(74) Attorney, Agent, or Firm — BakerHostetler

(57) ABSTRACT

This invention relates to a method for the prevention of cardiovascular disease, a formulation for the prevention of cardiovascular disease, the use of specified active principals for the manufacture of such a formulation for use in the method and to a method of preparing said formulation. The formulation of the present invention is a combination of active principals for use in the prevention of cardiovascular disease, notably ischaemic heart disease (including heart attacks) and stroke among the general adult population.

10 Claims, 6 Drawing Sheets

(56) References Cited

OTHER PUBLICATIONS

Law et al., "Value of low dose combination treatment with blood pressure lowering drugs: analysis of 354 randomized trials", BMJ, Jun. 2003, 326, 8 pages.
Relman, "Textbook of National Medicine", Book Review: Textbook of Natural Medication, http://www.quackwatch.org/01QuackeryRelatedTopics/Naturopathy/relman1.html,Jan. 2001, 4 pages.
Rodgers, "A Cure for Cardiovascular Disease", BMJ, Jun. 2003, 326, 1407-1408.
Smith, "Editor's Choice: The most Important BMJ for 50 years", BMJ, 326, Jun. 2003, 1 page.
Spaulding et al., "Chemical Abstract 129:339684", Circulation, 1998, 98(8), 757-765.
U.S. Food and Drug Administration, "Overview of Dietary Supplements", Jan. 2001, FDA/CFSAN Overview of Dietary Supplements, http://www.cfsan.fda.gov/~dms/ds-oview/html, 18 pages.
Uchida et al., "Inhibitory Effects of Condensed Tannins on Angiotensin Converting Enzyme", Japan J. Pharmacology., 1987, 43(242), 5 pages.
Wald et al., "A Strategy to Reduce Cardiovascular Disease by more than 80%", BMJ, Jun. 2003, 326, 6 pages.
Wald et al., "Does Breathing Other People's Tobacco Smoke Cause Lung Cancer", British Medical Journal, Nov. 1986, 293, 1217-1222.
White, "Polypill to Fight Cardiovascular Disease", BMJ, Oct. 2003, 327, p. 809.

\* cited by examiner

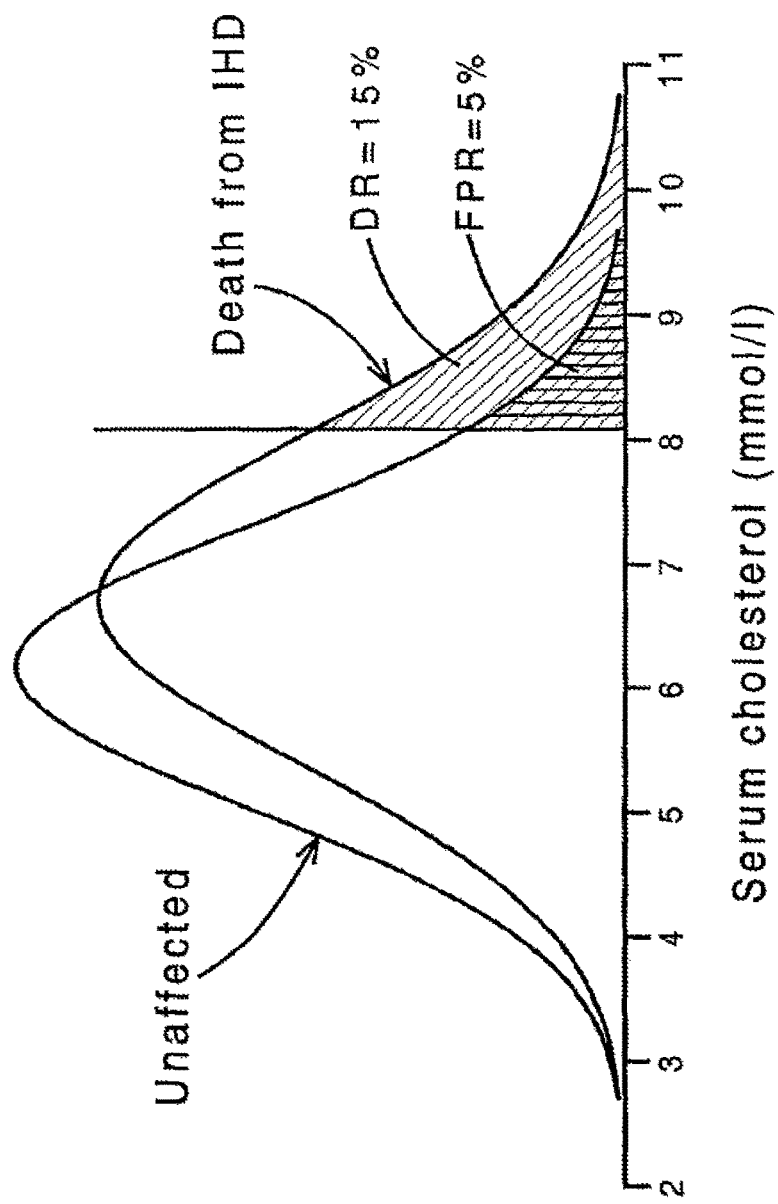

FORMULATION FOR THE PREVENTION OF CARDIOVASCULAR DISEASE

RELATED APPLICATIONS

The present application is a continuation of pending U.S. patent application Ser. No. 10/257,429, "Formulation for the Prevention of Cardiovascular Disease," filed on May 6, 2003. That pending application is a national stage filing of PCT Application No. PCT/GB01/01618, filed Apr. 10, 2001. That PCT application claimed priority to Great Britain Application No. 0008791.6, filed on Apr. 10, 2000 and to Great Britain Application No. 0100548.7, filed on Jan. 9, 2001. All of the foregoing applications are incorporated herein by reference in their entireties for any and all purposes.

This invention relates to a method for the prevention of cardiovascular disease, a formulation for the prevention of cardiovascular disease, the use of specified active principals for the manufacture of such a formulation for use in the method and to a method of preparing said formulation.

Cardiovascular disease, such as ischaemic heart disease (IHD) and stroke constitutes the main causes of death in most economically developed countries, accounting for about a third of all adult deaths. Table 1 shows the numbers of deaths from cardiovascular disease in England and Wales in 1998 in men and women over the age of 15, including death from heart disease and stroke and the smaller numbers of deaths from other cardiovascular causes that relate to the major cardiovascular risk factors. In total there are 200,000 deaths per year.

TABLE 1

|  | Men | | Women | |
| --- | --- | --- | --- | --- |
| Cause of death (ICD-9 code) | No of deaths | % of all deaths | No of deaths | % of all deaths |
| Ischaemic heart disease (410-4) | 66009 | 25% | 55024 | 19% |
| Stroke (430-8) | 21432 | 8% | 36046 | 13% |
| Heart failure (428)*, myocardial degeneration (429.1)* and hypertensive disease (401-5) | 5149 | 2% | 9172 | 2% |
| Aortic aneurysm (441) | 5829 | 2% | 3668 | 1% |
| Total | 98419 | 38% | 103914 | 36% |

*mostly due to ischaemic heart disease

The main environmental causes of these diseases, apart from cigarette smoking, are dietary and other lifestyle factors that increase the established risk factors of blood pressure, plasma or serum cholesterol (hereinafter simply referred to as serum cholesterol), plasma or serum homocysteine (hereinafter simply referred to as serum homocysteine), and impaire platelet function and coagulation. Realistic changes to lifestyle factors (dietary change, weight loss, increased exercise etc.) do not generally produce sufficient change in the cardiovascular risk factors to substantially reduce cardiovascular risk, so drug treatment to reduce the risk factors is commonly used.

The present policy for such drug treatment for reducing the incidence of cardiovascular diseases in the general population is based on intervention only when the level of one of these risk factors (especially blood pressure) is found to be particularly high (approximately the top 5% of the distribution in middle aged people and the top 10% in elderly people). Drugs have tended to be used specifically for the control of high values of each risk factor: an individual found to have what is regarded as high blood pressure but an average serum cholesterol concentration will be given treatment to lower the blood pressure but no treatment to lower the serum cholesterol. Drugs to alter platelet function (such as, for example, aspirin) and to lower serum homocysteine (such as, for example, folic acid) are rarely recommended for healthy persons. In persons who have had a non-fatal heart attack or stroke, treatment aimed at lowering blood pressure is given only if the blood pressure is at a level regarded as high (about top 10%), cholesterol lowering treatment is given if serum cholesterol is in roughly the upper half of the cholesterol distribution in the population, aspirin is routinely given, folic acid is generally not given.

The prevailing view that only extreme values of the clinical risk factors should be treated is reinforced by the commonly used terms "hypertension" (high blood pressure), "hypercholesterolaemia" (high serum cholesterol), "hyperhomocysteinaemia" (high serum homocysteine) implying that it is the increase from the normal value which is the damaging or dangerous condition. "Normal", as used herein, means having a level of risk factor (such as blood pressure, serum cholesterol, serum homocysteine) which is around the population average and therefore not judged to be high on the basis of conventional clinical practice or published professional guidelines (such as described, for example, in WO-A-97/38694 in the name of Merck & Co., Inc). "High" values have been defined in published professional guidelines as above a specified absolute value which is often close to the 90th or 95th centile of the risk factor in the population.

Under current clinical practice therefore, individuals found to have high values of the risk factors of cardiovascular disease are treated to reduce the risk factors (e.g. blood pressure or lipid level) to the so-called normal value, but no lower, by the application of one of many active principals known in the art. These high values may come to light as a result of routine health screening or as a result of an individual undergoing tests for a related or unrelated condition. Alternatively an individual who has had the misfortune of suffering from a cardiovascular insult such as a heart attack or stroke, may receive treatment for one or more of the risk factors associated with cardiovascular disease.

The proposition underlying this invention is that this policy and the practical clinical management of the policy is inefficient. There is, in fact, a considerable prejudice in the art which focuses clinical attention on the control of what are considered to be abnormally high risk factors once an individual presents with one or more high risk factors.

The present invention is based, in part, on the realisation of the following:

(1) Whilst cardiovascular disease is responsible for 37% of all deaths in England and Wales, treating individuals in the top 5% or so of a single risk factor distribution cannot make a significant impact on a group of diseases common enough to cause 37% of all deaths, even if the treatment were totally successful.

(2) Despite the aetiological importance of the cardiovascular risk factors, their effectiveness as screening tests in predicting risk in an individual is relatively weak (reference 10). Only about 20% of all deaths from heart disease and stroke occur in persons whose values of any of the risk factors lie in the top 10% of the distribution among persons in any specified age group. Since most cases of cardiovascular disease, such as myocardial infarction, occur in persons with risk factors close to the population average, seeking to identify persons who will have a heart attack or stroke by identifying only persons with especially high values of risk factors necessarily has a limited impact. Importantly, the average values of serum cholesterol, blood pressure and serum homocysteine in Britain and other Western populations where heart disease and stroke are common are high compared with the values in populations in which heart disease and stroke are rare. Also the distribution of values around this "high" average is relatively narrow. FIGS. 7 to 9 show the relative distributions of blood pressure and serum cholesterol in persons who subsequently die from a stroke or ischaemic heart disease, and the relative distributions of blood pressure and serum cholesterol in persons of the same age who do not subsequently die from these diseases. There is substantial overlap in the distributions indicating that the relevant risk factors (blood pressure or serum cholesterol) are poor discriminators of those who will and those who will not be affected. For example, if a serum cholesterol cut off level was selected that identified the 5% of people with highest serum cholesterol levels who did not die of ischaemic heart disease over the period of follow-up (false positive rate, FPR=5%), only 15% of persons who did die of ischaemic heart disease over the same period of follow-up would be correctly identified (detection rate DR, =15%). Thus, 85% of future deaths from ischaemic heart disease would be missed. The false positive rate (FPR) refers to the proportion of persons not developing the specified disease (stroke or ischaemic heart disease) whose value of the risk factor exceeds the specified value. The detection rate (DR) refers to the proportion of persons who do develop the disease whose values of the risk factor exceeds the specified value.

(3) Offering treatment to reduce the risk of a heart attack or stroke by reducing any one of these risk factors in isolation has a limited impact on the potential for reducing risk. Heart disease and stroke are common in Western countries because the average values of all the important risk factors are high and their effects, being independent of each other, interact in a multiplicative (or synergistic) manner. A combined treatment regimen aimed at changing several risk factors together is necessary to achieve a substantial reduction in risk.

(4) Present clinical practice fails to take account of the fact that the increased risk of cardiovascular disease with a particularly high level of one of the known risk factors represents merely that part of a dose response relationship lying above a population-determined normal level. The present inventors have demonstrated and discuss herein, that reducing the level of a risk factor below the accepted normal value gives rise to a concomitant reduction in the risk of cardiovascular disease. This finding and proof demonstrates that treatment by treating abnormally high levels of a risk factor is not efficient because there is no risk threshold. Even within the population "normal" range, further reduction of the risk factor continues to provide further reduction in the risk of cardiovascular disease. By detailed analysis of the literature and the application of techniques of biomedical statistics and meta-analysis, the present inventors have shown that there is no effective lower threshold of the risk of cardiovascular disease in relation to the level of a particular risk factor in economically developed populations, below which there is no further reduction in risk for further reductions in the risk factor.

For example, FIG. 1 is a logarithmic plot of the relative risk of suffering a stroke against the diastolic blood pressure. The advantage of using a log scale is that, if there is a strong link between the risk factor and the disease, there is a constant proportional reduction for a given unit change in the risk factor from any point on its distribution. The average diastolic blood pressure in the population is in the region of 85 mmHg (see FIGS. 7 and 8) and it can readily be seen that an individual exhibiting a higher blood pressure has an increased risk of suffering from a stroke. However, what is also apparent is that reducing the blood pressure, below that considered to be normal, by the same token reduces the risk at a similar rate on this logarithmic scale. Reductions in blood pressure among people with blood pressure which is not regarded as high, using blood pressure reducing agents in appropriate dosages, do not, or only very rarely, cause serious side effects, but do reduce the risk of cardiovascular disease. Significantly, the evidence is that the risk continues to be reduced across the whole range of blood pressure values found in the population and does not reach a threshold of risk at or around the average level in the population. Although as currently understood, the risk of cardiovascular disease increases when one of the risk factors exceeds the population average value, the risk does not remain constant below this value, but decreases with further decrease of the risk factor below the normal value. This is shown herein in FIGS. 1 to 5.

It can thus be seen that there are considerable advantages in reducing the level of risk factors such as blood pressure, serum lipid levels, platelet function levels and serum homocysteine levels below the normal levels exhibited in a given population, even where none of these levels exceeds the normal level in an individual. Any reduction in one or more of the risk factors of blood pressure, serum lipid levels, platelet function levels and serum homocysteine levels provides a significant reduction in the risk of cardiovascular disease, even if the levels in a particular individual are not high.

Effecting a reduction in the risk factor in individuals with a normal level of the risk factor is contrary to clinical practice, thus this proposal runs entirely contrary to the art.

The basis of the present invention is therefore that individuals should be treated irrespective of whether they exhibit particularly high values of any of the risk factors associated with cardiovascular disease or have a clinical history of cardiovascular disease, and that all risk factors should be changed. This is a considerable departure from the normal clinical practice and dogma.

The object of the present invention is to provide a method and formulations to address a significant clinical problem in the prior art. Current medical practice concentrates on the treatment of individuals who exhibit high levels of cardiovascular risk factors, such as high blood pressure, high serum lipid levels and high serum homocysteine levels, by treating these abnormal factors with various pharmaceuticals. The present invention demonstrates that this practice is inefficient since an extremely high proportion of the population is at risk of developing, and dying from cardiovascular disease with normal levels of or without knowing even if levels are above normal. By proposing reducing these levels in all patients, a significant improvement in the general health of the world's population can be achieved.

Combination drug therapies for the treatment of the risk factors of cardiovascular disease are known. The individual active principals used to treat the risk factors independently are well known and are, on occasion, used in combination. For example, in the treatment of high blood pressure, if an individual appears to fail to respond to a particular class of blood pressure reducing active principal, the dose of that drug will be increased to a higher dose, but if that still fails to give rise to the required blood pressure reduction, a second blood pressure lowering active principal may be administered in combination. In this clinical scenario, of course, the availability of a single formulation containing two blood pressure reducing active principals may not be useful as the whole clinical procedure requires careful dose adjustment in response to the condition of the patient. Recently, clinical practice has been to commence treatment of persons with abnormally high blood pressure with two different blood pressure lowering drugs in combination in some cases.

It has also been proposed to administer active principals against different risk factors in a single formulation. In WO-A-97/38694 (Merck & Co., Inc) for example, a lipid reducing drug, 3-hydroxy-3-methylglutaryl coenzyme A reductase inhibitor (HMG-CoA RI—a statin), is formulated together with folic acid (a homocysteine reducing drug) to make a combined formulation which is said to be more convenient for patient compliance as it is reasonably easy to add the small amount of folic acid necessary to an existing daily HMG-CoA RI unit dosage form. WO-A-97/38694 neither demonstrates nor suggests any additional physiological benefit of the combination. WO-A-97/38694 suggests very generally that other active agents may be added, listing a large and varied range of active agents with no specificity or indication of their intended purpose. Most significantly, there is no indication whatsoever of administering a combined formulation to individuals without measuring, or if measured regardless of the level, of any of the risk factors associated with cardiovascular disease. WO-A-98/11896 (Merck & Co., Inc) parallels this disclosure proposing a combination of an HMG-CoA RI with a platelet aggregation inhibitor. Neither the rationale for the combination nor any indication of advantage is disclosed. WO-A-98/19690 (Bristol-Myers Squibb Company) discloses combinations of folic acid (with or without vitamin B12) together with an agent selected to dilate the brain vasculature, this agent in some selections being a drug that is also in use as a blood pressure reducing agent. There are however critical distinctions from the present invention. The drugs are selected as vasodilating agents, not because they lower blood pressure. The folic acid is used only in persons with early Alzheimer's disease, not the general population and only in such persons with high homocysteine, not all such persons. The combination is not specified as a single preparation formulation. Spaulding et al Circulation (1998), 98(8), (757-765) describe clinical trials on the administration of aspirin and various ACE inhibitors to patients with ischaemic heart disease that is causing chronic heart failure. There are again critical distinctions from the present invention. The ACE inhibitor is used to control heart failure, not to prevent recurrent myocardial infarction or other recurrent ischaemic events; there is therefore no disclosure to synergy with the aspirin. The combination is to be used only in patients with heart failure, not in the general population. The combination is not specified as a single preparation formulation. Forbes et al Semin. Thromb. Hemostasis (1999), 25 Suppl., 55-59 describe combinations of one or other of two separate types of blood pressure reducing agents with a platelet aggregation inhibitor in trials on patients already exhibiting peripheral arterial obstructive disease or coronary artery disease. The trial concluded that the coadministration of the platelet aggregation agent did not interfere with the control of hypertension or angina. Again there are critical distinctions from the present invention. The calcium channel blocker was to be used to lower blood pressure only in patients selected as having particularly high blood pressure (hypertension), and the beta-blocker was to be used either to treat hypertension in the same way or to treat angina (that is to reduce the frequency of the pain). The combination is to be used only in persons with peripheral or coronary arterial disease, not the general population. The combination is not specified as a single preparation formulation.

According to the present invention there is provided a method for reducing the risk of cardiovascular disease comprising administering simultaneously, separately or sequentially, active principals from at least two of the following three categories:

i) at least one blood pressure lowering agent,
ii) at least one lipid-regulating agent, and
iii) at least one serum homocysteine lowering agent, with or without at least one platelet function altering agent, to an individual without measuring, or if measured regardless of the level of, one or more of the risk factors of cardiovascular disease selected from blood pressure, serum cholesterol, serum homocysteine or platelet function.

Alternatively, there is provided a method for reducing the risk of cardiovascular disease comprising administering simultaneously, separately or sequentially, at least one blood pressure lowering agent and at least one active principal from at least one of the following two categories:

i) at least one lipid-regulating agent, and
ii) at least one serum homocysteine lowering agent, with or without at least one platelet function altering agent, to an individual without measuring, or if measured regardless of the level of, one or more of the risk factors of cardiovascular disease selected from blood pressure, serum cholesterol, serum homocysteine or platelet function.

As used herein, the term "cardiovascular disease" means any atheromatous arterial disease, any non-syphilitic arterial aneurysm, and cerebral and subarachnoid haemorrhage. The cardiovascular system encompasses the entire vascular system of the body including the heart itself. Thus the term "cardiovascular disease" includes, but is not limited to, ischaemic heart disease (IHD), angina pectoris, coronary heart disease, stroke, transient ischaemic attacks, cerebrovascular disease, hypertensive disease, aortic aneurysm, peripheral arterial disease and retinal arterial disease.

The physiological effects of blood pressure lowering agents, lipid-regulating agents, platelet function altering agents and serum homocysteine lowering agents in reducing the risk of cardiovascular disease have been found to be independent of each other. The recognition of the combined effect of using these four different categories of drugs together is novel. At the preferred dosages of these drugs, the prevalence of the ratio of benefit to hazard, i.e. the ratio of the reduction in the incidence of cardiovascular disease to the prevalence of adverse effects of the drugs, is high. The estimation of the preventive effect of the formulation of the present invention and its application in a preventive setting is novel. In fact, a policy of treating a person in the general population, selected only on the basis of his or her age and sex, preventively against cardiovascular disease is contrary to the present policy for reducing the incidence of cardiovascular disease, which is based on intervention only if one or more risk factors are found to be high.

It is of considerable significance to the present invention that the method is applied to an individual without measuring, or if measured regardless of the level of, one or more of the risk factors of cardiovascular disease. As discussed above, only 5-10% of the population exhibit values of any of the risk factors of cardiovascular disease sufficiently high to warrant drug treatment under present clinical practice, but 37% of the population die from a cardiovascular disease. The effort involved in dealing with those individuals who have particularly high values of risk factors, in terms of medical analysis, clinician's time, the development of treatment programmes etc far outweighs the simple solution proposed here of reducing the risk factors in all persons above a specified age.

The correlation between age and the risk of cardiovascular disease is very strong as demonstrated in FIG. 6 herein. It is stronger than the relationship with risk factors of blood pressure, serum cholesterol and serum homocysteine. The data shown in FIG. 6 demonstrate that it is possible to determine a cut off age for routine treatment which may be independent of the need for every individual to undergo time consuming and costly tests.

Preferably, the method is applied to an individual above a predetermined age, for example an individual who may have no clinical symptoms of cardiovascular disease, the only criterion being that he or she is above a predetermined age. The predetermined age will vary from population to population according to the incidence of cardiovascular disease or according to the age distribution of cases (which depends on patterns of diet, smoking and other factors). The predetermined age can be determined simply by determining the age above which 95% of the deaths from ischaemic heart disease or stroke occur. Typically the predetermined age is from 45 to 65. The age by which 5% of all deaths from heart disease and stroke have occurred in England and Wales is about 55 for men and about 65 for women. Thus, most preferably, the method is applied to an individual above the age of 55 for males and above the age of 65 for females, based on England and Wales mortality data, and in other European countries the predetermined age would be similar. Alternatively, for simplicity, a single age preferably from 45 to 65, for example about 55, may be used for both men and women.

Alternatively, the method may be used when an individual's annual risk of ischaemic heart disease and stroke, calculated from their age, sex and measurable risk factors including blood pressure, serum cholesterol, serum homocysteine and smoking history, exceeds a predetermined value (such as for example 2% per year). The predetermined age may be determined using known statistical analyses based on data obtained from the population in which the individual resides. Preferably, the method is applied to individuals in the population above the age for the gender above which 95% of the deaths due to ischaemic heart disease or stroke occur.

The method may also be applied to an individual who has previously been diagnosed as having had the clinical symptoms of cardiovascular disease, irrespective of age.

Although the active principals may be administered simultaneously, separately or sequentially, preferably the active principals are administered simultaneously in a single dosage form. This is a major departure from present clinical practice. Present practice is to offer treatment (with the exception of aspirin) if the value of a particular risk factor is particularly high, and then to treat the risk factor that is high (even though risk of disease may be high and this would respond to the lowering of all risk factors).

For all of the active principals, the dosage is selected to maximise the reduction of risk of cardiovascular disease whilst minimising undesirable side effects. The dose will depend on the active principal concerned. The preferred doses are calculated to be at levels optimising the ratio of benefit to hazard, i.e. the ratio of reduction of the risk of cardiovascular disease to the risk of adverse effects of the administered agent. This optimisation is well within the scope of the skilled person with the benefit of appropriate experimental trials. The most preferred doses for lipid-regulating agents are within the therapeutic range recommended by the British National Formulary of March 2000 (see Table 2). The most preferred doses for platelet function altering agents are at the lower end of the therapeutic range recommended by the British National Formulary of March 2000 (see Table 2) (for example about 75 mg/day of aspirin). The most preferred doses for blood pressure lowering agents are half of the doses at the lower end of the therapeutic range recommended in the British National Formulary of March 2000 (see Table 2). The most preferred dose of folic acid is about 0.8 mg/day.

TABLE 2

| BNF Section | Active Principal | BNF Recommended Dose | Most Preferred Daily Dose |
| --- | --- | --- | --- |
| 2.2.1 Thiazide-like diuretics | bendroflume-thiazide/ bendrofluazide | hypertension, 2.5 mg in the morning, higher doses rarely necessary | about 1.25 mg |
| | chlorthalidone | hypertension, 25 mg in the morning, increased to 50 mg if necessary | about 12.5 mg |
| | cyclopenthia-zide | hypertension, initially 250 µg daily in the morning, increased if necessary to 500 µg daily | about 125 µg |
| | hydrochloro-thiazide | hypertension, 25 mg daily, increased to 50 mg daily if necessary; in some patients (especially the elderly) an initial dose of 12.5 mg daily may be sufficient | about 12.5 mg |
| | indapamide | 2.5 mg in the morning | about 1.25 mg |
| | mefruside | initially 25-50 mg in the morning, maintenance 25 mg daily or on alternate days | about 12.5 mg |
| | metolazone | hypertension, initially 5 mg in the morning, maintenance 5 mg on alternate days | about 2.5 mg on alternate days |
| | polythiazide | usually 1-4 mg daily, in hypertension 500 µg daily may be adequate | about 1 mg |
| | xipamide | hypertension, 20 mg in the morning | about 10 mg |
| 2.4 Beta blockers | propranolol hydrochloride | by mouth, hypertension, initially 80 mg twice daily, increased at weekly intervals as required, maintenance 160-320 mg daily | about 80 mg |

TABLE 2-continued

| BNF Section | Active Principal | BNF Recommended Dose | Most Preferred Daily Dose |
|---|---|---|---|
| | acebutolol | hypertension, initially 400 mg once daily or 200 mg twice daily, increased after 2 weeks to 400 mg twice daily if necessary | about 200 mg |
| | atenolol | by mouth, hypertension, 50 mg daily (higher doses rarely necessary) | about 25 mg |
| | betaxolol hydrochloride | 20 mg daily (elderly patients 10 mg), increased to 40 mg if required | about 10 mg |
| | bisoprolol fumarate | usual dose 10 mg daily (5 mg may be adequate in some patients), max. recommended dose 20 mg daily | about 5 mg |
| | carvedilol | hypertension, initially 12.5 mg once daily, increased after 2 days to usual dose of 25 mg once daily, if necessary may be further increased at intervals of at least 2 weeks to max. 50 mg daily in single or divided doses; elderly initial dose of 12.5 mg daily may provide satisfactory control | about 12.5 mg |
| | celiprolol hydrochloride | 200 mg once daily in the morning, increased to 400 mg once daily if necessary | about 100 mg |
| | labetalol hydrochloride | by mouth, initially 100 mg (50 mg in elderly) twice daily with food, increased at intervals of 14 days to usual dose of 200 mg twice daily, up to 800 mg daily in 2 divided doses (3-4 divided doses if higher), max. 2.4 g daily | about 200 mg |
| | metoprolol tartrate | by mouth, hypertension, initially 100 mg daily, maintenance 100-200 mg daily in 1-2 doses | about 50 mg |
| | nadolol | hypertension, 80 mg daily, increased at weekly intervals if required, max. 240 mg daily | about 40 mg |
| | nebivolol | 5 mg daily; elderly initially 2.5 mg daily, increased if necessary to 5 mg daily | about 2.5 mg |
| | oxprenolol hydrochloride | hypertension, 80-160 mg daily in 2-3 divided doses, increased as required, max. 320 mg daily | about 40 mg |
| | pindolol | hypertension, initially 5 mg 2-3 times daily or 15 mg once daily, increased as required at weekly intervals, usual maintenance 15-30 mg daily, max. 45 mg daily | about 7.5 mg daily |
| | timolol maleate | hypertension, initially 5 mg twice daily or 10 mg once daily, gradually increased if necessary to max. 60 mg daily (given in divided doses above 20 mg daily) | about 5 mg |
| 2.5.1 Vasodilator antihypertensive drugs | hydralazine hydrochloride | by mouth, hypertension, 25 mg twice daily, increased to usual max. 50 mg twice daily | about 25 mg daily |
| | minoxidil | initially 5 mg (elderly 2.5 mg) daily in 1-2 doses, increased by 5-10 mg every 3 or more days, max. usually 50 mg daily | about 12.5 mg |
| 2.5.5.1 ACE inhibitors | captopril | hypertension, used alone initially 12.5 mg twice daily; if used in addition to diuretic or in elderly initially 6.25 mg twice daily (first dose at bedtime); usual maintenance dose 25 mg twice daily; max. 50 mg twice daily (rarely three times daily in severe hypertension) | about 25 mg daily |
| | cilazapril | hypertension, initially 1-1.25 mg once daily (initial dose reduced in those receiving a diuretic, in the elderly, in renal impairment and in severe hepatic impairment - consult product literature), usual maintenance dose 2.5-5 mg daily, max. 5 mg daily renovascular hypertension, initially 250-500 μg once daily, then adjusted according to response | about 1.25 mg |
| | enalapril maleate | hypertension, used alone, initially 5 mg once daily; if used in addition to diuretic, in elderly patients or in renal impairment initially 2.5 mg daily; usual | about 5 mg |

TABLE 2-continued

| BNF Section | Active Principal | BNF Recommended Dose | Most Preferred Daily Dose |
|---|---|---|---|
| | | maintenance dose 10-20 mg once daily; in severe hypertension may be increased to max. 40 mg daily | |
| | fosinopril | hypertension, initially 10 mg daily, increased if necessary after 4 weeks, usual dose range 10-40 mg (doses over 40 mg not shown to increase efficacy) | about 5 mg |
| | imidapril hydrochloride | initially 5 mg daily before food; if used in addition to diuretic, in elderly, in patients with heart failure, angina or cerebrovascular disease, or in renal or hepatic impairment, initially 2.5 mg daily; if necessary increase dose at intervals of at least 3 weeks; usual maintenance dose 10 mg once daily; max. 20 mg daily (elderly 10 mg daily) | about 5 mg |
| | lisinopril | hypertension, initially 2.5 mg daily; usual maintenance dose 10-20 mg daily; max. 40 mg daily | about 5 mg |
| | moexipril hydrochloride | used alone, initially 7.5 mg once daily; if used in addition to diuretic, with nifedipine, in elderly, in renal or hepatic impairment, initially 3.75 mg once daily; usual range 15-30 mg once daily; doses above 30 mg daily not shown to increase efficacy | about 7.5 mg |
| | perindopril | hypertension, initially 2 mg daily (before food), usual maintenance dose 4 mg once daily, max. 8 mg daily | about 2 mg |
| | quinapril | hypertension, initially 10 mg once daily; with a diuretic, in elderly, or in renal impairment initially 2.5 mg daily; usual maintenance dose 20-40 mg daily in single or 2 divided doses; up to 80 mg daily has been given | about 10 mg |
| | ramipril | hypertension, initially 1.25 mg daily, increased at intervals of 1-2 weeks, usual range 2.5-5 mg once daily, max. 10 mg daily | about 1.25 mg |
| | trandolapril | hypertension, initially 500 μg once daily, increased at intervals of 2-4 weeks, usual range 1-2 mg once daily, max. 4 mg daily | about 0.5 mg |
| 2.5.5.2 Angiotensin II receptor antagonists | candesartan cilexetil | initially 4 mg (2 mg in hepatic and renal impairment) once daily adjusted according to response, usual maintenance dose 8 mg once daily, max. 16 mg once daily | about 4 mg |
| | irbesartan | 150 mg once daily, increased if necessary to 300 mg once daily (in haemodialysis or in elderly over 75 years, initial dose of 75 mg once daily may be used) | about 75 mg |
| | losartan potassium | usually 50 mg once daily (elderly over 75 years, moderate to severe renal impairment, intravascular volume depletion, initially 25 mg once daily), if necessary increased after several weeks to 100 mg once daily | about 25 mg |
| | telmisartan | 40 mg once daily, increased if necessary to 80 mg once daily | about 20 mg |
| | valsartan | usually 80 mg once daily (elderly over 75 years, mild to moderate hepatic impairment, moderate to severe renal impairment, intravascular volume depletion, initially 40 mg once daily), if necessary increased after at least 4 weeks to 160 mg daily (80 mg daily in hepatic impairment) | about 40 mg |
| 2.6.2 Calcium channel blockers | amlodipine besilate | hypertension, initially 5 mg once daily, max. 10 mg once daily | about 2.5 mg |
| | diltiazem hydrochloride | see individual preparations | |
| | felodipine | hypertension, initially 5 mg (elderly 2.5 mg) daily in the morning, usual maintenance 5-10 mg once daily, doses above 20 mg daily rarely needed | about 2.5 mg |

TABLE 2-continued

| BNF Section | Active Principal | BNF Recommended Dose | Most Preferred Daily Dose |
|---|---|---|---|
| | isradipine | 2.5 mg twice daily (1.25 mg twice daily in elderly, hepatic or renal impairment), increased if necessary after 3-4 week to 5 mg twice daily (exceptionally up to 10 mg twice daily), maintenance 2.5 or 5 mg once daily may be sufficient | about 2.5 mg daily |
| | lacidipine | initially 2 mg as a single daily dose, preferably in the morning; increased after 3-4 weeks to 4 mg daily, then if necessary to 6 mg daily | about 2 mg |
| | lercanidipine hydrochloride | initially 10 mg once daily; increased if necessary after at least 2 weeks to 20 mg daily | about 5 mg |
| | nicardipine hydrochloride | initially 20 mg 3 times daily, increased after at least 3 days to 30 mg 3 times daily (usual range 60-120 mg daily) | about 30 mg daily |
| | nifedipine | see individual preparations | |
| | nisoldipine | initially 10 mg daily, preferably before breakfast; if necessary increase at intervals of at least 1 week; max. 40 mg daily | about 5 mg |
| 2.9 Platelet function altering drugs | aspirin | 75-300 mg daily | about 75 mg |
| | clopidrogrel | 75 mg once daily | about 75 mg |
| | dipyridamole | by mouth: 300-600 mg daily in 3-4 divided doses before food modified-release preparations, see individual preparations by intravenous injection: diagnostic only, consult product literature | about 300 mg |
| | ticlopidine hydrochloride | 250 mg twice daily | about 500 mg daily |
| 2.12 Lipid-regulating drugs | colestyramine | lipid reduction (after initial introduction over 3-4 weeks) 12-24 g daily in water (or other suitable liquid) in single or up to 4 divided doses, up to 36 g daily if necessary child 6-12 years see product literature | about 12 g |
| | colestipol hydrochloride | 5 g 1-2 times daily in liquid, increased if necessary at intervals of 1-2 months to max. of 30 g daily (in single or 2 divided doses) | about 5 g |
| | bezafibrate | see individual preparations | |
| | ciprofibrate | 100 mg daily | about 100 mg |
| | clofibrate | over 65 kg, 2 g daily (50-65 kg, 1.5 g daily) in 2 or 3 divided doses | about 2 g |
| | fenofibrate | see individual preparations | |
| | gemfibrozil | 1.2 g daily, usually in 2 divided doses; range 0.9-1.5 g daily | about 1.2 g |
| | atorvastatin | primary hypercholesterolaemia and combined hyperlipidaemia, usually 10 mg once daily familial hypercholesterolaemia, initially 10 mg daily, increased at intervals of 4 weeks to 40 mg once daily; if necessary further increased to max. 80 mg once daily (or combined with anion-exchange resin in heterozygous familial hypercholesterolaemia) | about 10 mg |
| | cerivastatin sodium | initially 100 μg once daily in the evening, increased by increments of 100 μg at intervals of not less than 4 weeks to max. 300 μg once daily (200 μg daily in moderate to severe renal impairment) | about 200 μg |
| | fluvastatin | initially 20-40 mg daily in the evening; usual range 20-40 mg daily in the evening, adjusted at intervals of 4 weeks; up to 40 mg twice daily may be required | about 20 mg |
| | pravastatin sodium | usual range 10-40 mg once daily at night, adjusted at intervals of not less than 4 weeks | about 20 mg |
| | simvastatin | hyperlipidaemia, 10 mg daily at night, adjusted at intervals of not less than 4 | about 20 mg |

TABLE 2-continued

| BNF Section | Active Principal | BNF Recommended Dose | Most Preferred Daily Dose |
|---|---|---|---|
| | | weeks; usual range 10-40 mg once daily at night coronary heart disease, initially 20 mg once daily at night | |

For drugs used to lower blood pressure, the dose of an active principal is below the lower therapeutic dosage for the indication of the active principal. As used herein, the term "therapeutic dosage" is intended to refer to the commonly used dose in clinical practice for the treatment of high levels of the risk factor or for the treatment of cardiovascular disease by the separate active principal. The most preferred doses for blood pressure lowering agents are half of the doses at the lower end of the therapeutic range recommended in the British National Formulary of March 2000. This is in order to maximise the therapeutic benefit of the combination of agents, while minimising the risks of adverse effects of the individual agents. An analysis of randomised placebo controlled trials of the individual drugs (given in the references) shows that with half the present recommended dose the reduction in blood pressure is only 20% lower than with the full recommended dose, while the reduction in adverse effects is much greater. Most preferably, the dose of a blood pressure lowering agent is about half the recommended dose (or, where a range of doses is given, half of the recommended dose at the lower end of the recommended therapeutic range) for the blood pressure lowering agent.

Preferably the blood pressure lowering agent is a diuretic, a beta blocker, an ACE inhibitor, an angiotension-II receptor antagonist, a vasodilator antihypertensive drug, and/or a calcium-channel blocker. More preferably the blood pressure lowering agent is a diuretic, and/or a beta blocker, and/or an ACE inhibitor.

Preferably the diuretic is a thiazide or thiazide-like diuretic. Preferably the thiazide or thiazide-like diuretic is hydrochlorothiazide, chlorthalidone, indapamide, bendroflumethiazide, chlorothiazide, metolazone, cyclopenthiazide, polythiazide, mefruside, or xipamide. Most preferably the thiazide or thiazide-like diuretic is hydrochlorothiazide. Thiazide or thiazide-like diuretics are categorised in Section 2.2.1 of the British National Formulary of March 2000 and other equivalent national formularies or pharmacopoeias, such as for example the "Physicians Desk Reference" (PDR) and "Martindale: The Extra Pharmacopoeia" (Reynolds J E F (ed.), London, Royal Pharmaceutical Society, 1996). Preferably the hydrochlorothiazide is administered in an amount of from about 2.5 mg to about 62.5 mg per day; more preferably the hydrochlorothiazide is administered in an amount of from about 5 mg to about 37.5 mg per day; most preferably the hydrochlorothiazide is administered in an amount of about 12.5 mg per day.

Preferably the beta blocker is a $\beta_1$-selective adrenoceptor antagonist; preferably the $\beta_1$ selective adrenoceptor antagonist is atenolol, bisoprolol, betaxolol, metoprolol, celiprolol, or acebutolol. Alternatively the beta blocker is a non-selective beta-adrenoceptor antagonist; preferably the non-selective beta-adrenoceptor antagonist is pindolol, propranolol, oxprenolol, sotalol, timolol, or nadolol. Alternatively the beta blocker is a drug with combined β- and α-adrenoceptor blocking action; preferably this drug is carvedilol, or labetolol. Most preferably the beta blocker is atenolol. Beta blockers are categorised in Section 2.4 of the British National Formulary of March 2000 and in other equivalent national formularies or pharmacopoeias. Preferably the atenolol is administered in an amount of from about 5 mg to about 125 mg per day; more preferably the atenolol is administered in an amount of from about 10 mg to about 75 mg per day; most preferably the atenolol is administered in an amount of about 25 mg per day.

Preferably the ACE inhibitor is enalapril, perindopril, captopril, cilazapril, trandolapril, fosinopril, quinapril, lisinopril, ramipril, or moexipril. Most preferably the ACE inhibitor is enalapril. ACE inhibitors are categorised in Section 2.5.5.1 of the British National Formulary of March 2000 and in other equivalent national formularies or pharmacopoeias. Preferably the enalapril is administered in an amount of from about 1 mg to about 25 mg per day; more preferably the enalapril is administered in an amount of from about 1.5 mg to about 15 mg per day; most preferably the enalapril is administered in an amount of about 5 mg per day.

Preferably the angiotension-II receptor antagonist is losartan, valsartan, candesartan, eprosartan, irbesartan or telmisartan. More preferably the angiotension-II receptor antagonist is losartan. Angiotension-II receptor antagonists are categorised in Section 2.5.5.2 of the British National Formulary of March 2000 and in other equivalent national formularies or pharmacopoeias. Preferably the losartan is administered in an amount of from about 5 mg to about 125 mg; more preferably the losartan is administered in an amount of from about 10 mg to about 75 mg per day; most preferably the losartan is administered in an amount of about 25 mg per day.

Preferably the vasodilator antihypertensive drug is hydralazine. Vasodilator antihypertensive drugs are categorised in Section 2.5.1 of the British National Formulary of March 2000 and in other equivalent national formularies or pharmacopoeias. Preferably the hydralazine is administered in an amount of from about 2.5 mg to about 62.5 mg per day; more preferably the hydralazine is administered in an amount of from about 5 mg to about 37.5 mg per day; most preferably the hydralazine is administered in an amount of about 12.5 mg per day.

Preferably the calcium-channel blocker is amlodipine, diltiazem, felodipine, isradipine, lacidipine, lercanidipine, nicardipine, nifedipine, nimodipine or nisoldipine. More preferably the calcium-channel blocker is amlodipine. Calcium-channel blockers are categorised in Section 2.6.2 of the British National Formulary of March 2000 and in other equivalent national formularies or pharmacopoeias. Preferably the amlodipine is administered in an amount of from about 0.5 mg to about 12.5 mg per day; more preferably the amlodipine is administered in an amount of from about 0.8 mg to about 7.5 mg per day; most preferably the amlodipine is administered in an amount of about 2.5 mg per day. Preferably the amlodipine is administered as the maleate or besilate.

Preferably the formulation of the present invention comprises more than one blood pressure lowering agent. More preferably the formulation comprises two blood pressure lowering agents. Most preferably the formulation comprises three blood pressure lowering agents. Preferably the blood pressure lowering agents will be independently selected from a diuretic, a beta blocker, an ACE inhibitor, an angiotensin II receptor antagonist, and a calcium channel blocker. More preferably the blood pressure lowering agents will be independently selected from a diuretic, a beta blocker, and an ACE inhibitor.

Preferably the lipid-regulating agent is a 3-hydroxy-3-methylglutaryl coenzyme A (HMG CoA) reductase inhibitor, also called a statin. Preferably the statin is atorvastatin, simvastatin, cerivastatin, fluvastatin, or pravastatin. More preferably the statin is atorvastatin or simvastatin. Most preferably the statin is atorvastatin. Lipid-regulating drugs are categorised in Section 2.12 of the British National Formulary of Mach 2000 and in other equivalent national formularies or pharmacopoeias. Preferably the atorvastatin is administered in an amount of from about 2 mg to about 50 mg per day; more preferably the atorvastatin is administered in an amount of from about 3 mg to about 30 mg per day; most preferably the atorvastatin is administered in an amount of about 10 mg per day. Preferably the simvastatin is administered in an amount of from about 2 mg to about 60 mg per day; more preferably the atorvastatin is administered in an amount of from about 3 mg to about 40 mg per day; most preferably the atorvastatin is administered in an amount of from about 10 mg to about 20 mg per day.

Preferably the platelet function altering agent is aspirin, ticlopidine, dipyridamole, clopidogrel, or a glycoprotein IIb/IIIa receptor inhibitor such as abciximab, or a non-steroidal anti-inflammatory drug such as ibuprofen. Most preferably the platelet function altering agent is aspirin. Platelet function altering agents are categorised in Section 2.9 of the British National Formulary of March 2000 and in other equivalent national formularies or pharmacopoeias. Non-steroidal anti-inflammatory drugs are categorised in Section 10.1.1 of the British National Formulary of March 2000 and in other equivalent national formularies or pharmacopoeias. Preferably the aspirin is administered in an amount of from about 15 mg to about 500 mg per day; more preferably the aspirin is administered in an amount of from about 25 mg to about 250 mg per day; most preferably the aspirin is administered in an amount of about 75 mg per day.

Preferably the serum homocysteine lowering agent is folic acid, vitamin B6, or vitamin B12, or a combination of two or three of these. Most preferably the serum homocysteine lowering agent is folic acid. Preferably the folic acid is administered in an amount of from about 0.2 mg to about 4 mg per day; more preferably the folic acid is administered in an amount of from about 0.4 mg to about 2 mg per day; most preferably the folic acid is administered in an amount of about 0.8 mg per day.

Most preferably the formulation used in the method of the invention comprises:
   i) about 12.5 mg hydrochlorothiazide, about 25 mg atenolol, and about 5 mg enalapril as blood pressure lowering agents,
   ii) about 10 mg atorvastatin as lipid-regulating agent,
   iii) about 75 mg aspirin as platelet function altering agent, and
   iv) about 0.8 mg folic acid as serum homocysteine lowering agent.

Alternatively the formulation used in the method of the invention comprises:
   i) about 12.5 mg hydrochlorothiazide, about 25 mg atenolol, and about 5 mg enalapril as blood pressure lowering agents,
   ii) about 10-20 mg simvastatin as lipid-regulating agent,
   iii) about 75 mg aspirin as platelet function altering agent, and
   iv) about 0.8 mg folic acid as serum homocysteine lowering agent.

Alternatively the formulation used in the method of the invention comprises:
   i) about 12.5 mg hydrochlorothiazide, about 25 mg atenolol, and about 2.5 mg amlodipine maleate as blood pressure lowering agents,
   ii) about 10-20 mg simvastatin as lipid-regulating agent,
   iii) about 75 mg aspirin as platelet function altering agent, and
   iv) about 0.8 mg folic acid as serum homocysteine lowering agent.

Alternatively the formulation used in the method of the invention comprises:
   i) about 12.5 mg hydrochlorothiazide, about 2.5 mg amlodipine maleate, and about 5 mg enalapril as blood pressure lowering agents,
   ii) about 10-20 mg simvastatin as lipid-regulating agent,
   iii) about 75 mg aspirin as platelet function altering agent, and
   iv) about 0.8 mg folic acid as serum homocysteine lowering agent.

Optionally the method of the present invention further comprises an active principal from a fifth category comprising anti-oxidants. Preferably the antioxidant is vitamin E.

Preferably the active principals are administered orally to a patient.

The use of the formulation may reduce the risk of cardiovascular disease by at least 80%. Preferably, the use of the formulation reduces the risk of cardiovascular disease by at least 50%, more preferably the use of the formulation reduces the risk of cardiovascular disease by at least 60%, even more preferably the use of the formulation reduces the risk of cardiovascular disease by at least 70%, most preferably the use of the formulation reduces the risk of cardiovascular disease by at least 80%.

The invention further provides formulations for use in the treatment of cardiovascular disease.

In a further aspect of the invention there is provided a formulation comprising at least two blood pressure lowering agents, each selected from a different physiological mode of action selected from a diuretic, a beta blocker, an angiotensin converting enzyme (ACE) inhibitor, an angiotensin II receptor antagonist, and a calcium channel blocker, and an active principal from at least two of the following three categories:
   i) at least one lipid-regulating agent,
   ii) at least one platelet function altering agent, and
   iii) at least one serum homocysteine lowering agent.

As used herein, physiological mode of action refers to the way in which an active principal exerts its activity on the body of a patient.

Current clinical practice is to treat individual risk factors as they present themselves in any given person. Thus, under current clinical practice, individuals presenting clinical risk factors of cardiovascular disease are treated to return the risk factors (e.g. blood pressure or lipid level) to the so-called normal value, but no lower, by the application of one of many active principals known in the art.

Preferably the formulation has active principals from two of the three categories, i), ii) and iii). More preferably the formulation has active principals from categories i) and ii). Most preferably the formulation comprises active principals from all three categories, i), ii), iii). Optionally the formulation comprises more than one active principal from one or more of the three categories.

The diuretic, the beta blocker, the ACE inhibitor, the angiotensin II receptor antagonist and the calcium channel blocker are preferably those referred to above, preferably in the doses referred to above. Similarly the lipid-regulating agent, the platelet function altering agent, and the serum homocysteine lowering agent are preferably those referred to above, preferably in the dose referred to above.

Under current clinical practice for the use of blood pressure lowering agents, such a formulation in, for example, a single dosage form would not be considered useful given the clinical practice of only providing an additional blood pressure reducing active principal if a first blood pressure reducing active principal, or at most two such drugs in combination, fails to provide the desired lowering of blood pressure. The present inventors have demonstrated that the effect of different classes of the blood pressure reducing active principals act independently and therefore combinations of two or more blood pressure reducing active principals in a single dose produce an additive effect, greatly improving efficacy. Moreover the use of lipid-regulating, platelet function altering and serum homocysteine altering agents in combination with blood pressure lowering agents to reduce a person's overall risk of cardiovascular disease runs contrary to current clinical practice.

It will be understood that providing a formulation where the dose of a blood pressure lowering agent is below the lower therapeutic dose for the blood pressure lowering agent is contrary to the art. The lower therapeutic dose for any given blood pressure lowering agent is readily determinable by the skilled addressee by reference to the British National Formulary of March 2000 in common use in the country of this patent at the time of writing.

There is further provided a formulation comprising active principals from at least two of the following three categories:
 i) at least one blood pressure lowering agent,
 ii) at least one platelet function altering agent, and
 iii) at least one serum homocysteine lowering agent,
 wherein the dose of the blood pressure lowering agent, if present, is below the lower therapeutic dosage for the blood pressure lowering agent.

Alternatively there is provided a formulation comprising at least one blood pressure lowering agent and active principals from at least one of the following three categories:
 i) at least one lipid-regulating agent,
 ii) at least one platelet function altering agent, and
 iii) at least one serum homocysteine lowering agent,
 wherein the dose of the blood pressure lowering agent, if present, is below the lower therapeutic dosage for the blood pressure lowering agent.

Again, the blood pressure reducing agent, the lipid-regulating agent, the platelet function altering agent, and the serum homocysteine lowering agent are preferably those referred to above, preferably in the doses referred to above.

In a preferred mode of operation, the present invention relates to treating individuals irrespective of the levels of any risk factors and without any test whatsoever. Preferably selection is based only on a person's age, sex and history of existing cardiovascular disease. In this mode, the avoidance of deleterious side effects is important. Accordingly, it is appropriate for the formulation to contain a lower amount of the blood pressure lowering agent than the normal clinical dose. This is entirely contrary to the state of the art, which provides formulations containing active principals at or around the full therapeutic dose.

In another aspect of the invention there is provided a formulation comprising active principals from at least three of the following four categories:
 i) at least one blood pressure lowering agent,
 ii) at least one lipid-regulating agent,
 iii) at least one platelet function altering agent, and
 iv) at least one serum homocysteine lowering agent.

Again, the blood pressure reducing agent, the lipid-regulating agent, the platelet function altering agent, and the serum homocysteine lowering agent are preferably those referred to above, preferably in the dose referred to above.

Preferably, the formulation contains a dose of a blood pressure lowering agent which is about half the recommended dose at the lower end of the recommended therapeutic range for the blood pressure lowering agent.

Most preferably, the formulation comprises:
 i) about 12.5 mg hydrochlorothiazide, about 25 mg atenolol, and about 5 mg enalapril as blood pressure lowering agents,
 ii) about 10 mg atorvastatin as a lipid-regulating agent,
 iii) about 75 mg aspirin as a platelet function altering agent, and
 iv) about 0.8 mg folic acid as a serum homocysteine lowering agent.

Alternatively, the formulation comprises:
 i) about 12.5 mg hydrochlorothiazide, about 25 mg atenolol, and about 5 mg enalapril as blood pressure lowering agents,
 ii) about 10-20 mg simvastatin as a lipid-regulating agent,
 iii) about 75 mg aspirin as a platelet function altering agent, and
 iv) about 0.8 mg folic acid as a serum homocysteine lowering agent.

Alternatively the formulation used in the method of the invention comprises:
 i) about 12.5 mg hydrochlorothiazide, about 25 mg atenolol, and about 2.5 mg amlodipine maleate as blood pressure lowering agents,
 ii) about 10-20 mg simvastatin as lipid-regulating agent,
 iii) about 75 mg aspirin as platelet function altering agent, and
 iv) about 0.8 mg folic acid as serum homocysteine lowering agent.

Alternatively the formulation used in the method of the invention comprises:
 i) about 12.5 mg hydrochlorothiazide, about 2.5 mg amlodipine maleate, and about 5 mg enalapril as blood pressure lowering agents,
 ii) about 10-20 mg simvastatin as lipid-regulating agent,
 iii) about 75 mg aspirin as platelet function altering agent, and
 iv) about 0.8 mg folic acid as serum homocysteine lowering agent.

In a still further aspect of the invention, there is provided the use of active principals from two or more of the following three categories:
 i) at least one blood pressure lowering agent,
 ii) at least one lipid-regulating agent, and
 iii) at least one serum homocysteine lowering agent,
 with or without at least one platelet function altering agent, for the manufacture of a formulation for administration to an individual without measuring, or if measured regardless of the level of, one or more of the risk factors of cardiovascular disease selected from blood pressure, serum cholesterol, serum homocysteine and platelet function.

Alternatively, there is provided the use of at least one blood pressure lowering agent and at least one active principal from at least one of the following two categories:
 i) at least one lipid-regulating agent, and
 ii) at least one serum homocysteine lowering agent,
with or without at least one platelet function altering agent, for the manufacture of a formulation for administration to an individual without measuring, or if measured regardless of the level of, one or more of the risk factors of cardiovascular disease selected from blood pressure, serum cholesterol, serum homocysteine and platelet function.

The formulation of the present invention can be administered by oral or parenteral routes, including intravenous, intramuscular, subcutaneous, transdermal (including patches), airway (aerosol), rectal and topical (including buccal and sublingual) administration. Preferably the formulation of the present invention is provided in a form suitable for oral administration. For oral administration, the formulation of the present invention is preferably in the form of a tablet, a capsule, a pill, a powder, granules, a solution, or a suspension.

Tablets for oral use may include the components mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate, glyceryl distearate, cellulose acetate phthalate, hydroxypropylcellulose phthalate, polyvinylacetate phthalate, methylmethacrylate polymer, a polymer mixture such as Eudragit®, a cellulose derivative, zein, wax or similar material, or any other dissolvable coat, to delay absorption in the gastrointestinal tract.

Capsules for oral use include hard gelatin capsules in which the components are mixed with a solid diluent, and soft gelatin capsules wherein the components are mixed with water or an oil such as peanut oil, liquid paraffin or olive oil. The components may be compartmentalised within a capsule to prevent contact during storage.

Preferably one or more of the active principals is enteric coated before tableting or encapsulation. Preferably the platelet function altering agent, in particular aspirin, consists of enteric coated beads or granules before tableting or encapsulation. Preferably the whole tablet or capsule is enteric coated. Preferably the enteric coating material comprises cellulose acetate phthalate, hydroxypropylcellulose phthalate, polyvinylacetate phthalate, methylmethacrylate polymer or a polymer mixture such as Eudragit®.

Preferably one or more of the active principals is delay-release coated before tableting or encapsulation. Preferably the platelet function altering agent, in particular aspirin, consists of delay-release coated beads or granules before tableting or encapsulation. Preferably the whole tablet or capsule is delay-release coated. Preferably the delay-release coating material comprises cellulose acetate phthalate, hydroxypropylcellulose phthalate, polyvinylacetate phthalate, methylmethacrylate polymer, a polymer mixture such as Eudragit®, a cellulose derivative, zein, glyceryl monostearate or glyceryl distearate.

Preferably the delay-release tablet is formed from a matrix comprising wax or similar material. Alternatively, the delay-release tablet is an erodable tablet formed from a cellulose derivative or similar material. Alternatively, the delay-release tablet is coated with a dissolvable coat.

The desired dose is preferably presented once daily, but may be dosed as two, three, four or more sub-doses administered at appropriate intervals throughout the day. Preferably the active principals are present in the tablet, capsule, pill, powder, granules, solution, or suspension in amounts suitable for administration once, twice, or three times per day. More preferably the active principals are present in the tablet, capsule, pill, powder, granules, solution, or suspension in amounts suitable for administration once per day.

All preferred dosages are calculated to be at levels optimising the ratio of benefit to hazard, i.e. the ratio of reduction of the risk of cardiovascular disease to the risk of adverse effects of the administered agent.

Preferably the formulation is used as a medicament. More preferably the formulation is used as a medicament for the prevention of cardiovascular disease. Most preferably the formulation is used as a medicament for the prevention of ischaemic heart disease. Alternatively, most preferably the formulation is used as a medicament for the prevention of stroke or transient ischaemic attack.

Preferably the formulation is used in men and women above a specified age for the reduction in the risk of cardiovascular disease. Alternatively the formulation is used in men and women with an estimated risk of cardiovascular disease above a specified level, wherein the risk is determined by measurement of risk factors used in conjunction with a person's age and sex. The formulation is also used in persons with a clinical history of coronary artery disease or cardiovascular disease irrespective of age or the values of risk factors.

Preferably the use of the formulation of the present invention reduces the risk of cardiovascular disease by at least 80%.

The present invention further provides the use of the formulation of the present invention for the manufacture of a medicament for the prevention of cardiovascular disease, preferably the manufacture of a medicament for the prevention of ischaemic heart disease or stroke. Preferably the medicament is used in men and women above specified ages for the reduction in the risk of cardiovascular disease. Alternatively the medicament is used in men and women with an estimated risk of cardiovascular disease above a specified level, wherein the risk is determined by measurement of risk factors used in conjunction with a person's age and sex.

The present invention further provides a method of preparing the formulation of the present invention, comprising the steps of:
 i) mixing the two or more active principals optionally with one or more pharmaceutically acceptable excipients, and
 ii) forming the mixture into a tablet, a capsule, a pill, a powder, granules, a solution, or a suspension suitable for oral administration to a patient.

BRIEF DESCRIPTION OF THE DRAWINGS

FIG. 9 is a graph showing the relative distributions of serum cholesterol (in mmol/l) in persons who subsequently die from ischaemic heart disease and in persons of the same age who do not subsequently die from ischaemic heart disease (If the false positive rate (FPR) is 5%, then the detection rate (DR) is 15%).

For each of the factors that affect the risk of heart disease and stroke and that can be favourably altered by drug therapy (blood pressure, serum cholesterol, serum homocysteine and platelet function), the relationships with heart disease and stroke are continuous across the range of values in Western populations. The higher the value of the risk factor, the greater is the risk of heart disease and stroke; an increased risk is not confined to persons with unusually high values of the risk factors. For each of the four risk factors, this continuous proportionate relationship has been established by two classes of evidence.

Figure 1:
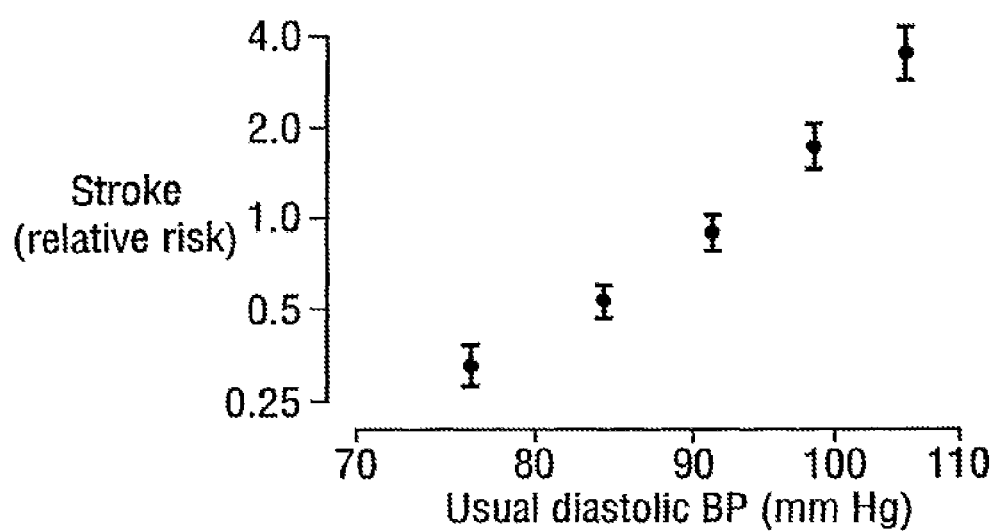
FIG. 1 is a graph showing the relative risk (95% confidence limits) of stroke according to blood pressure (reference 1). Both vertical and horizontal axes are plotted on logarithmic scales.
Figure 2:
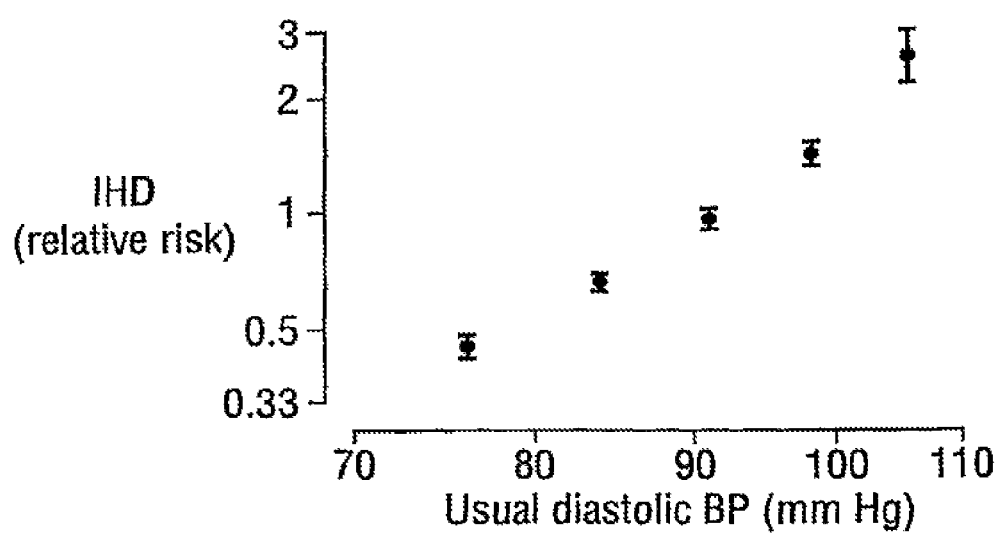
FIG. 2 is a graph showing the relative risk (95% confidence limits) of ischaemic heart disease (IHD) according to blood pressure (reference 1). Both vertical and horizontal axes are plotted on logarithmic scales.
Figure 3:
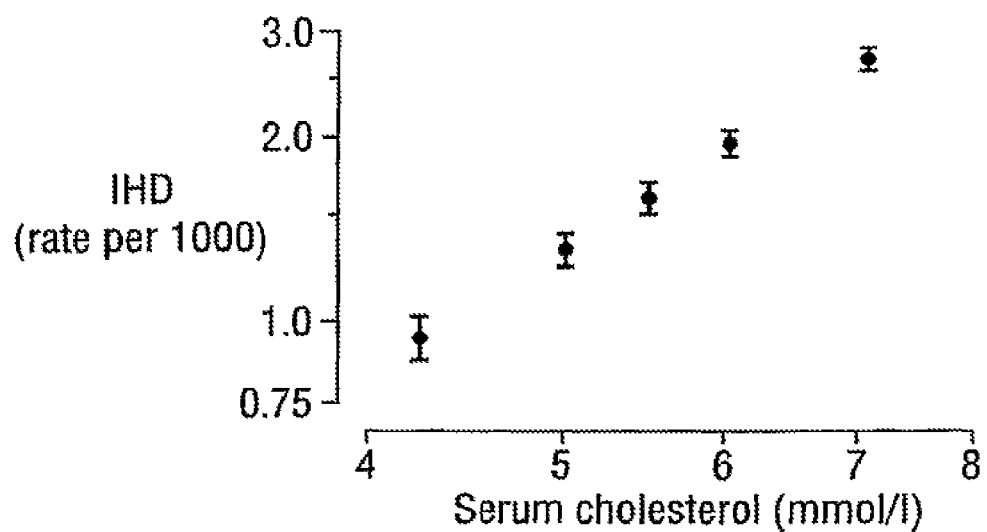
FIG. 3 is a graph showing the mortality (95% confidence limits) from ischaemic heart disease according to serum cholesterol (reference 2). Both vertical and horizontal axes are plotted on logarithmic scales.
Figure 4:
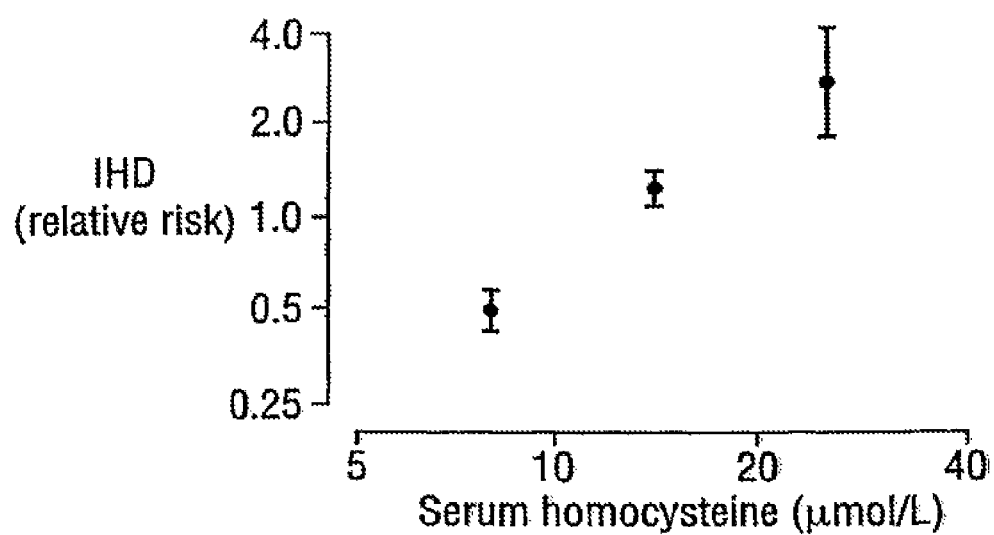
FIG. 4 is a graph showing the relative risk (95% confidence limits) of ischaemic heart disease according to serum homocysteine (reference 3). Both vertical and horizontal axes are plotted on logarithmic scales.
Figure 5:
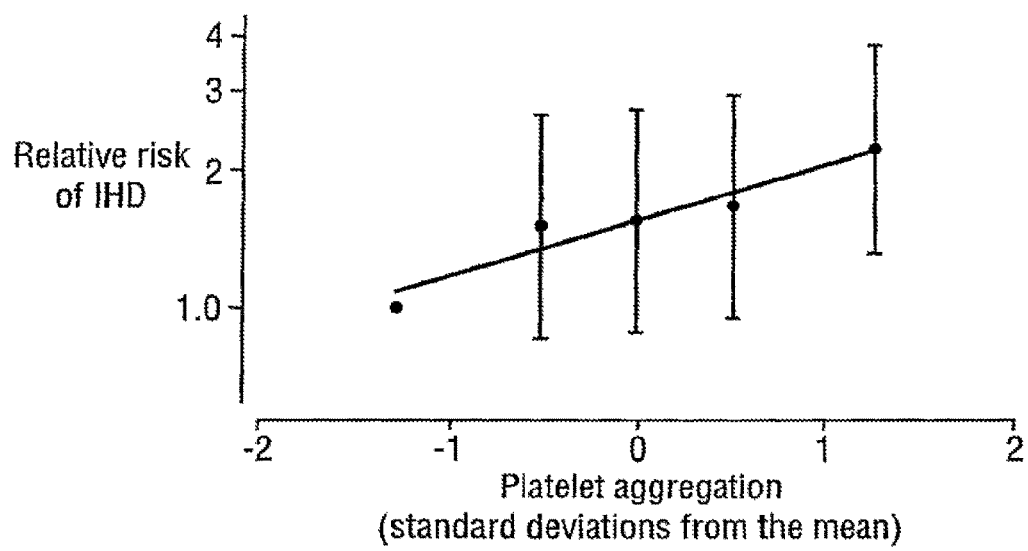
FIG. 5 is a graph showing the relative risk (95% confidence limits) of ischaemic heart disease according to platelet aggregation (reference 4). The vertical axis is plotted on a logarithmic scale.
Figure 6:
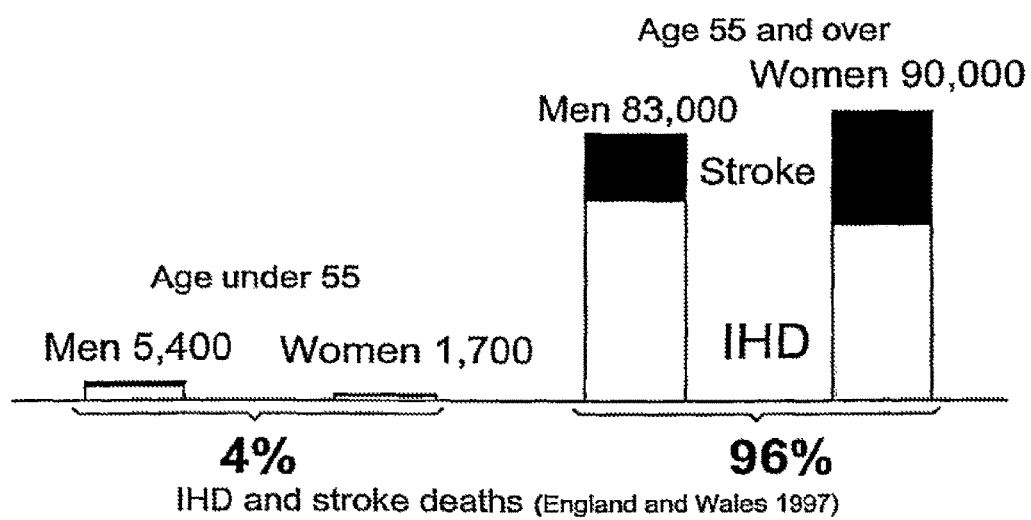
FIG. 6 is a bar chart depicting the deaths from cardiovascular disease above and below the age of 55 for men and for women.
Figure 7:
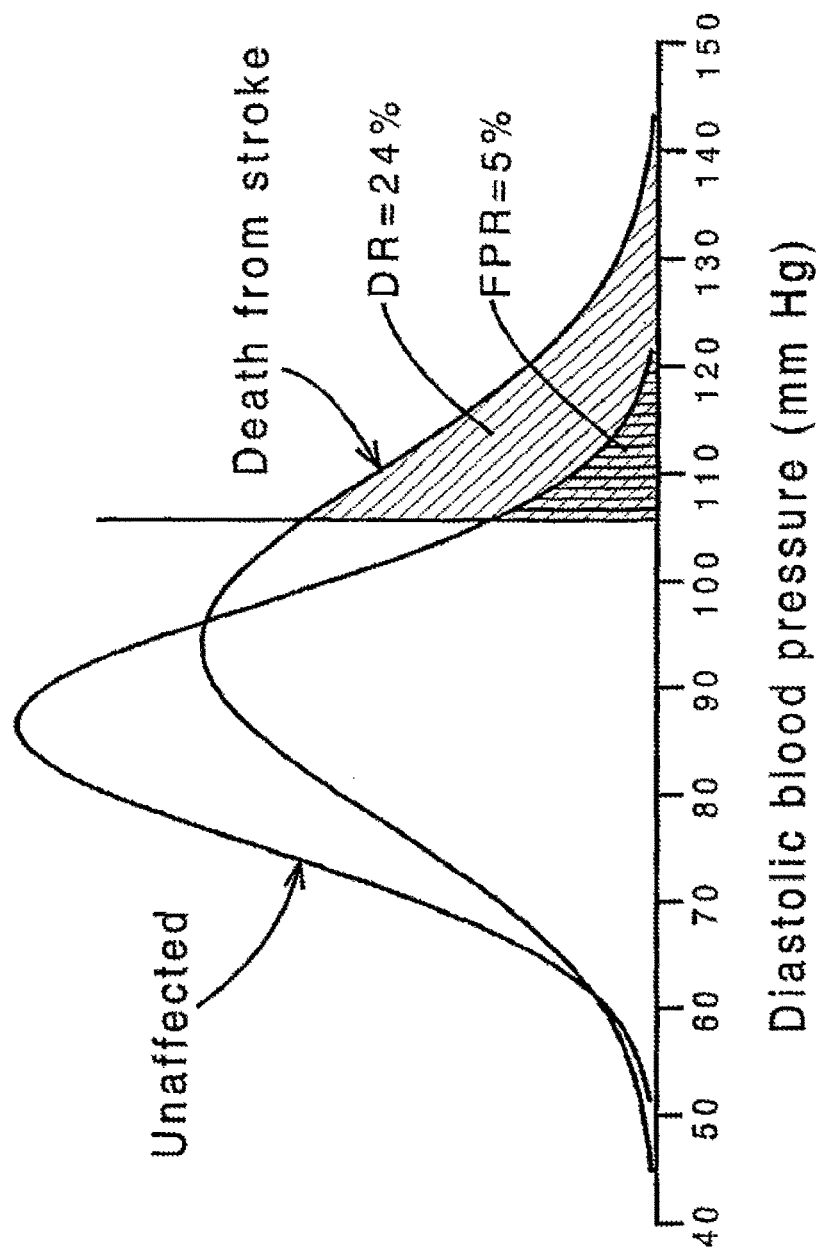
FIG. 7 is a graph showing the relative distributions of diastolic blood pressure (in mmHg) in persons who subsequently die from a stroke and in persons of the same age who do not subsequently die from a stroke (If the false positive rate (FPR) is 5%, then the detection rate (DR) is 15%).
Figure 8:
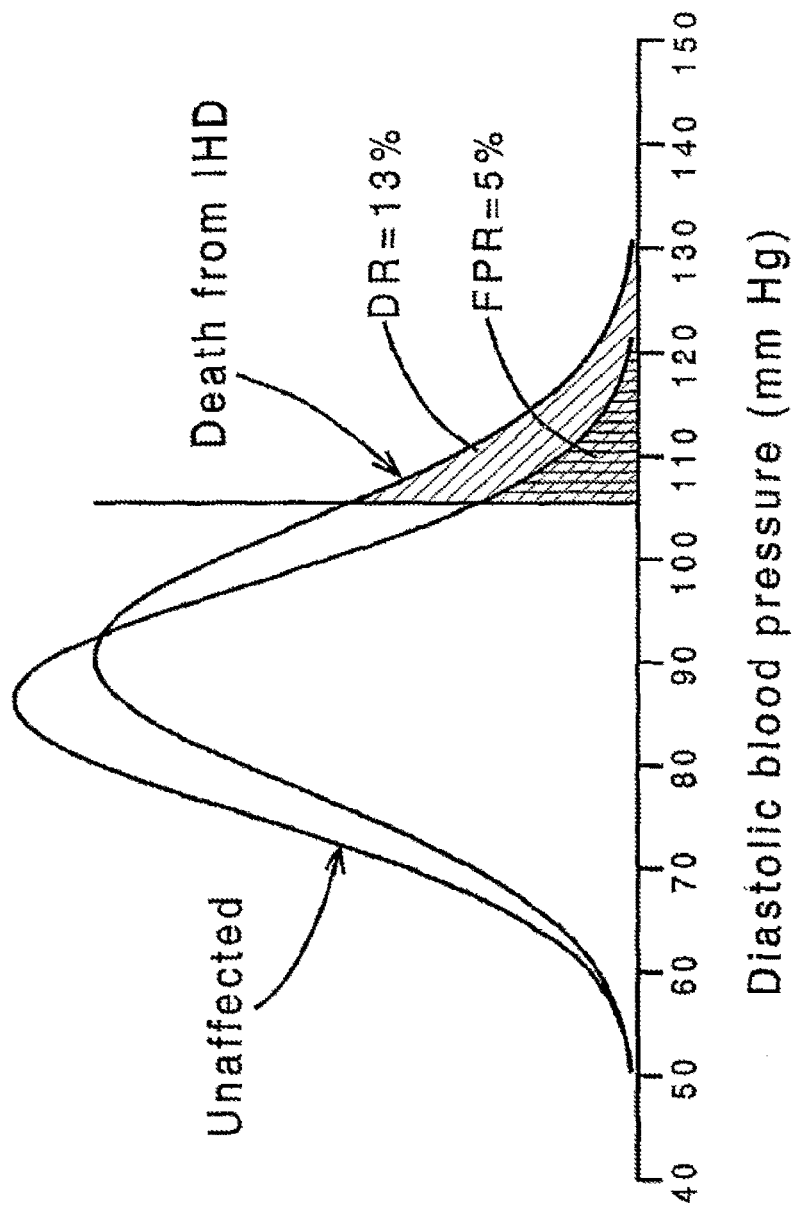
FIG. 8 is a graph showing the relative distributions of diastolic blood pressure (in mmHg) in persons who subsequently die from ischaemic heart disease and in persons of the same age who do not subsequently die from ischaemic heart disease (If the false positive rate (FPR) is 5%, then the detection rate (DR) is 13%).

The first is a series of epidemiological studies in which measurements were made on a large number of persons and the values of the risk factors correlated against the subsequent incidence of heart attacks and stroke. FIGS. 1 to 5 show five sets of data on the relationships between cardiovascular risk factors and the incidence of ischaemic heart disease or stroke (namely, blood pressure and stroke, blood pressure and ischaemic heart disease, serum cholesterol and ischaemic heart disease, serum homocysteine and ischaemic heart disease, body mass index and ischaemic heart disease). The data are either from single large epidemiological studies or from studies in which the data from several smaller studies have been combined (references 1-4). The study populations have been divided into subgroups (five equal subgroups in three of the five relationships shown) according to ranked values of the risk factor, as shown on the horizontal axes. Incidence, on the vertical axes, is plotted on a logarithmic (or proportional) scale. In each case the relationship is well described by a straight line, and in FIGS. 1 to 4 the 95% confidence intervals on each of the estimates of incidence are inconsistent with a relationship that is markedly non-linear. The linear relationship indicates that given a change in one of the risk factors from any point on the distribution is associated with a constant proportionate change in the risk of heart disease and stroke.

The second class of evidence is randomised controlled trials in which medication was given to lower the risk factors. Randomised trials have shown that drugs that lower blood pressure produced the same proportionate reduction in the incidence of heart attacks and stroke, irrespective of whether the starting blood pressure was high or average (reference 5). Similarly, randomised trials have shown that drugs that lower serum cholesterol have produced the same proportionate reduction in the incidence of heart attacks and stroke, irrespective of whether the starting concentration of serum cholesterol was high or average (references 6-7). Randomised trials have shown that aspirin reduces the incidence of heart attacks and stroke in both high risk and low risk persons (reference 8) (platelet function was not measured in the aspirin trials). For serum homocysteine no randomised trials are yet available, but evidence is available on persons with different genetic disorders that increase serum homocysteine concentration to varying extents; the increase in risk of cardiovascular disease in the different disorders is commensurate with the increase in serum homocysteine (references 3, 9).

Because of this continuous proportionate relationship between each of these risk factors and the incidence of ischaemic heart disease and stroke, it would be appropriate to alter all four of them in a person whose risk is high for any reason—a particularly high blood pressure for example, some genetic predisposition (recognised or unrecognised), or simply increasing age. The decision that preventive treatment in an individual is worthwhile should be based on the person's overall level of risk of a heart attack or stroke, not on the level of a particular risk factor. Because of the constant proportionate relationship, the benefit will be greater in those whose risk is greater. The preferred approach therefore is to use all these agents to lower risk in persons whose existing overall risk is above a specified level. There is a need for a treatment strategy and a formulation that will combine the benefits of all of them, while minimising the occurrence of adverse effects (thereby increasing the potency:hazard ratio), and for the formulation to be available on a wide scale to individuals above a specified risk of having a major cardiovascular episode.

As stated above, the classical cardiovascular risk factors (blood pressure, serum cholesterol, serum homocysteine) are poor screening tests in discriminating between persons who do and do not develop cardiovascular disease. A more discriminatory determinant of risk is age: the incidence of myocardial infarction and stroke doubles with every eight years of advancing age. By contrast, a doubling of risk occurs over a wide span of the distributions of the four risk factors (references 3, 4, 11, 12) (approximately from the 5th centile of the distributions to the 50th, or from the 50th to the 95th). Sex is also an important determinant of risk—the incidence in women at any age is about the same as that in men ten years younger. However, the single most important determinant of a person's risk is the presence of existing disease: in a person who has already had a heart attack or a stroke, for example, the risk of death from cardiovascular disease is about 5% per year, irrespective of age, sex, or the values of the risk factors.

The formulation of the present invention contains various components all designed to reduce the risk of cardiovascular disease by changing different predisposing risk factors. The formulation is prepared in doses that maximise efficacy and minimise adverse effects. Preferably the formulation is offered to all persons above a certain age or risk cut-off. The start of treatment could be determined firstly by a person's history of existing disease: any person with a history of previous myocardial infarction or angina, or a previous stroke or transient ischaemic attack, irrespective of age, sex, or the values of the risk factors, would be at sufficient risk to take the integrated formulation. In persons with no history of past disease, the start of treatment could be determined simply by a person's age and sex so that all men above a specified age (say 55 years) would take the integrated formulation each day and women could follow the same strategy but start at an older age (say at age 65 years). Alternatively, treatment could begin when a person's annual risk of ischaemic heart disease and stroke, calculated from their age, sex, and easily measurable risk factors (for example smoking, blood pressure and body mass index) was above a specified value. Such a policy would be substantially more effective than the current practice of using pharmacological agents specific for a single risk factor and doing so only in individuals with high values of that risk factor or in individuals who have already suffered a major cardiovascular episode. The proposed new approach also takes into account, where current practice does not, that a history of previous cardiovascular disease and, in healthy persons, age are far more discriminatory measures of high risk than any of the cardiovascular risk factors.

Table 3 shows the risk factors altered by each of these drugs, the amount by which each one is changed on average by the preferred dosage, and the resulting expected reduction in the risks of ischaemic heart disease and stroke. Table 3 also shows that all the drugs in combination reduce the risk of ischaemic heart disease by an estimated 88% and of stroke by an estimated 86%. This combined estimate is based on the fact that the effects on the four different risk factors are unrelated and so the expected effects of changing each one will be independent of each other. This expectation is supported by two classes of evidence. First, epidemiological studies (in which the values of the risk factors were measured in many thousands of persons and the distribution of values examined in those who subsequently died of heart disease and stroke and those who did not) have shown that blood pressure, serum cholesterol, platelet function, and serum homocysteine are largely independent of each other in relation to the risk of cardiovascular disease (references 2, 3, 6, 218). For example the ratio of the risk of a disease event in persons with high blood pressure and the risk in persons with low blood pressure is similar, irrespective of the values of serum cholesterol and other risk factors. Second, some randomised clinical trials have used combinations of two of the drugs (for example beta blockers and aspirin) in patients with ischaemic heart disease and have shown that the effects are independent (that is, the relative risk in patients who took two drugs (compared with the risk in those who took none) was similar to the relative risk in persons taking one of the drugs multiplied by the relative risk in persons taking the other drug). Accordingly, the effect of the different drugs in combination in Table 3 has been calculated by multiplying the effects of each as shown in footnotes h and j.

TABLE 3

The constituent drugs in the proposed combined formulation, the cardiovascular risk factors that each alter, the amount by which each factor would be changed, and the resulting expected reduction in risk of ischaemic heart disease and stroke.

| Drug | Example (daily dose) | Associated physiological variable (reduction produced by drug) | Expected reduction in risk of: | |
|---|---|---|---|---|
| | | | ischaemic heart disease | stroke |
| Thiazide diuretic | Hydrochlorothiazide (12.5 mg) | Blood pressure (12 mmHg diastolic)$^a$ | 43%$^b$ | 63%$^b$ |
| Beta blocker | Atenolol (25 mg) | | | |
| ACE inhibitor | Enalapril (5 mg) | | | |
| Statin | Atorvastatin (10 mg) | Serum cholesterol (1.8 mmol/l)$^c$ | 61%$^d$ | 50%$^d$ |
| Aspirin | Aspirin (75 mg) | Platelet aggregation | 38%$^e$ | 15%$^e$ |
| Folic acid | Folic acid (0.8 mg) | Plasma/serum homocysteine (3 μmol/l)$^f$ | 15%$^g$ | 10%$^g$ |
| All drugs in combination | | | 88%$^h$ | 86%$^j$ |

$^a$Estimate obtained by us from an analysis of the blood pressure reduction according to dose in 187 randomised placebo controlled trials of thiazide or thiazide-like diuretics, beta-blockers and ACE inhibitors (references 13-199).
$^b$Reduction in risk to be expected from the blood pressure reduction of 12 mmHg diastolic, from published analyses of cohort studies and randomised controlled trials of blood pressure and ischaemic heart disease and stroke (references 1, 5).
$^c$From published randomised placebo controlled trials of atorvastatin (reference 200).
$^d$The reduction in risk to be expected from the serum cholesterol reduction of 1.8 mmol/l, from published analyses of cohort studies and randomised controlled trials of serum cholesterol and ischaemic heart disease, and of randomised controlled trials of serum cholesterol reduction and stroke (references 6, 201, 202).
$^e$Estimate obtained by us from an analysis of the results of 14 randomised controlled trials of aspirin in dosage of 50-100 mg daily and the incidence of ischaemic heart disease and stroke (references 203-216).
$^f$A meta-analysis of published randomised controlled trials of folic acid in doses between 1 mg and 5 mg showed that the maximum reduction in plasma homocysteine is 3 μmol/l and that this maximum reduction is produced by a folic acid dose of 1 mg (reference 217); an unpublished randomised controlled trial performed by us has suggested that a folic acid dose of 0.8 mg is the lowest dose that produces this maximum reduction in homocysteine.
$^g$The reduction in risk to be expected from the reduction in plasma homocysteine of 3 μmol/l from the results of cohort studies of homocysteine and cardiovascular disease (references 3, 9).
$^h$100% − [(100% − 43%) × (100% − 61%) × (100% − 38%) × (100% − 15%)] = 88%.
$^j$100% − [(100% − 63%) × (100% − 50%) × (100% − 15%) × (100% − 10%)] = 86%.

Table 4 shows estimates of the prevalence of adverse effects from each of the medications when taken in the preferred dose (shown as the difference in prevalence between treated and placebo groups in randomised trials). The dose of each medication has been chosen to maximise the ratio of benefit to hazard. It is recognised that some persons taking a combination of six drugs would develop adverse effects that were unacceptable. The adverse effects attributable to each of the component medications would be made clear to persons taking the combined formulation and alternative formulations omitting one or more of the component ingredients, with or without a substitute ingredient, would be available for persons unable to tolerate one component.

expected from the blood pressure reductions, from published analyses of cohort studies and randomised controlled trials of blood pressure and ischaemic heart disease and stroke (references 1, 5).

It will be understood that the present invention has been described above by way of example only. The examples are

TABLE 4

The estimated prevalence of adverse effects of each of the six drugs to be included in the integrated formulation

| Drug | Example (daily dose) | Commonest adverse effects | Prevalence of any adverse effect in randomised trials (treated minus control) | Prevalence of serious adverse effects (those that warranted withdrawal from randomised trial) (treated minus control) |
|---|---|---|---|---|
| Thiazide diuretic | Hydrochlorothiazide (12.5 mg) | dizziness, impotence, nausea | 1.4%[a] | 0.1%[a] |
| Beta blocker | Atenolol (25 mg) | cold extremities, fatigue, dizziness | 5.6%[a] | 0.9%[a] |
| ACE inhibitor | Enalapril (5 mg) | cough | 2.1%[a] | 0.2%[a] |
| Statin | Atorvastatin (10 mg) | — | 0.1% | <0.1% |
| Aspirin | Aspirin (75 mg) | bleeding, indigestion | 1.8%[b] | 0.7%[b] (mainly rectal or urinary bleeding) |
| Folic acid | Folic acid (0.8 mg) | — | <0.1% | <0.1% |

[a]Estimate obtained by us from an analysis of the prevalence of adverse effects according to dose in 187 randomised placebo controlled trials of thiazide diuretics, beta-blockers and ACE inhibitors (references 13-199).
[b]Estimate obtained by us from an analysis of the prevalence of adverse effects in 14 randomised placebo controlled trials of aspirin in dosage between 50 and 100 mg (references 203-216).

The doses of the first three drugs listed in Tables 3 and 4 (the drugs used to lower blood pressure) are half the present standard (or recommended) dose. Table 5 shows the reduction in blood pressure and in the incidence of ischaemic heart disease and stroke, and the prevalence of adverse effects, from using half standard dose (as in Tables 3 and 4) and from using the present standard (or recommended) dose. There is little loss of efficacy using half standard dose, but the prevalence of adverse effects is reduced by almost half. In other words, the ratio of benefit to hazard is greater. The preferred dose of aspirin is the dose generally used in the prevention of cardiovascular disease (75 mg/day); this is much less than the dose necessary to relieve pain.

TABLE 5

The combined effect of three drugs that lower blood pressure (a thiazide diuretic, a beta blocker and an ACE inhibitor) in lowering blood pressure, and reducing the incidence of ischaemic heart disease and stroke, together with the combined prevalence of adverse effects, according to whether the drugs are given in half standard dose or standard dose.

| | Half standard dose (preferred dose) | Standard dose |
|---|---|---|
| Reduction in diastolic blood pressure | 12 mmHg | 15 mmHg |
| Proportionate reduction in incidence of: | | |
| ischaemic heart disease | 43% | 50% |
| stroke | 63% | 71% |
| Prevalence of adverse effects | 9% | 16% |

Estimates were obtained by us from an analysis of the blood pressure reduction and prevalence of adverse effects according to dose in 187 randomised placebo controlled trials of thiazide diuretics, beta-blockers and ACE inhibitors (references 13-199). The corresponding reductions in incidence of ischaemic heart disease and stroke are those to be not intended to limit the scope of the invention. Various modifications and embodiments can be made without departing from the scope of the invention, which is defined by the following claims only.

REFERENCES

1. MacMahon S, Peto R, Cutler J, Collins R, Sorlie P, Neaton J, et al. Blood pressure, stroke and coronary heart disease. Part 1, prolonged differences in blood pressure: prospective observational studies corrected for the regression dilution bias. *Lancet* 1990; 335:765-74
2. Neaton J D, Wentworth D. Serum cholesterol, blood pressure, cigarette smoking, and death from coronary heart disease. *Arch Intern Med* 1992; 152:56-64
3. Wald N J, Watt H C, Law M R, Weir D G, McPartlin J, Scott J M. Homocysteine and ischaemic heart disease: results of a prospective study with implications on prevention. *Arch Intern Med* 1997
4. Law M R, Morris J K, Wald N J. Environmental tobacco smoke exposure and ischaemic heart disease: an evaluation of the evidence. *BMJ* 1997; 315:973-88
5. Collins R, Peto R, MacMahon S, Hebert P, Fiebach N H, Eberlein K A, et al. Blood pressure, stroke and coronary heart disease. Part 2, short-term reductions in blood pressure: overview of randomised drug trials in their epidemiological context. *Lancet* 1990; 335:827-38
6. Law M R, Wald N J, Thompson S G. By how much and how quickly does reduction in serum cholesterol concentration lower risk of ischaemic heart disease? *BMJ* 1994; 308:367-72
7. Scandinavian Simvastatin Survival Study Group. Baseline serum cholesterol and treatment effect in the Scandinavian Simvastatin Survival Study (4S). *Lancet* 1995; 345:1274-5

8. Antiplatelet Trialists' Collaboration. Collaborative overview of randomised trials of antiplatelet therapy-I: prevention of death, myocardial infarction, and stroke by prolonged antiplatelet therapy in various categories of patients. *BMJ* 1994; 308:81-106
9. Law M R. Lowering heart disease risk with cholesterol reduction: evidence from observational studies and clinical trials. European Heart Journal Supplements 1999; 1 (Suppl S): S3-S8
10. Wald N J, Hackshaw A K, Frost C D. When can a risk factor be used as a worthwhile screening test? *BMJ* 1999; 319:1562-5
11. Stamler J, Stamler R, Neaton J D. Blood pressure, systolic and diastolic, and cardiovascular risks. *Arch Intern Med* 1993; 153:598-615
12. Stamler J, Wentworth D, Neaton J D. Is relationship between serum cholesterol and risk of premature death from coronary heart disease continuous and graded? *JAMA* 1986; 256:2823-8
13. Petersen J R, Drabaek H, Gleerup G, Mehlsen J, Petersen L J, Winther K. ACE Inhibition with spirapril improves diastolic function at rest independent of vasodilation during treatment with spirapril in mild to moderate hypertension. *Angiology* 1996; 47:233-40
14. Burris J F, Weir M R, Oparil S, Weber M, Cady W J, Stewart W H. An assessment of diltiazem and hydrochlorothiazide in hypertension. *JAMA* 1990; 263:1507-12
15. Scholze J, Breitstadt A, Cairns V, Bauer B, Bender N, Priestley, et al. Ramipril and hydrochlorothiazide combination therapy in hypertension: a clinical trial of factorial design. *J Hypertens* 1993; 11:217-21
16. Frei M, Küster L, von Krosigk P G, Koch H, Küppers. Moxonidine and hydrochlorothiazide in combination: a synergistic antihypertensive effect. *J Cardiovasc Pharmacol* 1994; 24(Suppl 1):525-528
17. Goldberg M R, Rockhold F W, Offen W W, Dornseif B E. Dose-effect and concentration-effect relationships of pinacidil and hydrochlorothiazide in hypertension. *Clin Pharmacol Ther* 1989; 46:208-18
18. Muiesan G, Agabiti-Rosei E, Buoninconti R, Cagli V, Carotti A, Corea L, et al. Antihypertensive efficacy and tolerability of captopril in the elderly: comparison with hydrochlorothiazide and placebo in a multicentre, double-blind study. *J Hypertens* 1987; 5 (Suppl 5):5599-5602
19. Pool P E, Applegate W B, Woehler T, Sandall P, Cady W J. A randomized, controlled trial comparing diltiazem, hydrochlorothiazide, and their combination in the therapy of essential hypertension. *Pharmacotherapy* 1993; 13:487-93
20. Wing L M H, Arnolda L F, Harvey P J, Upton J, Molloy D, Bune A J C, et al. Lacidipine, hydrochlorothiazide and their combination in systolic hypertension in the elderly. *J Hypertens* 1997; 15:1503-10
21. Chalmers J P, Morris M J, Wing L M H, Cain M D, West M J, Graham J R, et al. Effects of enalapril and hydrochlorothiazide on blood pressure, renin-angiotensin system, and atrial natriuretic factor in essential hypertension: a double blind factorial cross-over study. *Aust NZ J Med* 1986; 16:475-80
22. Chalmers J P, Korner P I, Tiller D J, Bune A J, Steiner J D, West M J, et al. Double-blind factorial trial of prindolol and hydrochlorothiazide in hypertension. *Med J Aust* 1976; 1:650-3
23. Chalmers J, Horvath J, Tiller D, Bune A. Effects of timolol and hydrochlorothiazide on blood-pressure and plasma renin activity. *Lancet* 1976; 2:328-31
24. McCorvey E, Wright J T, Culbert J P, McKenney J M, Proctor J D, Annett M P. Effect of hydrochlorothiazide, enalapril, and propranolol on quality of life and cognitive and motor function in hypertensive patients. *Clinical Pharmacy* 1993; 12:300-5
25. Myers M G, de Champlain J. Effects of atenolol and hydrochlorothiazide on blood pressure and plasma catecholamines in essential hypertension. *Hypertension* 1983; 5:591-6
26. Jounela A J, Lilja M, Lumme J, Morlin C, Hoyem A, Wessel-aas T, et al. Relation between low dose of hydrochlorothiazide, antihypertensive effect and adverse effects. *Blood Press* 1994; 3:231-5
27. Pool J, Cushman W C, Saini R K, Nwachuku C E, Battikha J P. Use of the factorial design and quadratic response surface models to evaluate the fosinopril and hydrochlorothiazide combination therapy in hypertension. *Am J Hypertens* 1997; 10:117-23
28. Canter D, Frank G J, Knapp L E, Phelps M, Quade M, Texter M. Quinapril and hydrochlorothiazide combination for control of hypertension: assessment by factorial design. *J Hum Hypertens* 1994; 8:155-62
29. Frishman W H, Bryzinski B S, Coulson L R, DeQuattro V L, Vlachakis N D, Mroczek W J, et al. A multifactorial trial design to assess combination therapy in hypertension. *Arch Intern Med* 1994; 154:1461-9
30. Zachariah P K, Messerli F H, Mroczek W. Low-dose bisoprolol/hydrochlorothiazide: an option in first-line, antihypertensive treatment. *Clin Ther* 1993; 15:779-87
31. Chrysant S G. Antihypertensive effectiveness of low-dose lisinopril-hydrochlorothiazide combination. *Arch Intern Med* 1994; 154:737-43
32. Fernández M, Madero R, González D, Camacho P, Villalpando J, Arriaga J. Combined versus single effect of fosinopril and hydrochlorothiazide in hypertensive patients. Hypertension 1994; 23 (Suppl I):1-207-10
33. Lacourcière Y, Arnott W. Placebo-controlled comparison of the effects of nebivolol and low-dose hydrochlorothiazide as monotherapies and in combination on blood pressure and lipid profile in hypertensive patients. *J Hum Hypertens* 1994; 8:283-8
34. Pordy R C. Cilazapril plus hydrochlorothiazide: improved efficacy without reduced safety in mild to moderate hypertension. *Cardiology* 1994; 85:311-22
35. Weir M R, Weber M A, Punzi H A, Serfer H M, Rosenblatt S, Cady W J. A dose escalation trial comparing the combination of diltiazem SR and hydrochlorothiazide with the monotherapies in patients with essential hypertension. *J Hum Hypertens* 1992; 6:133-8
36. Brown C L, Backhouse C I, Grippat J C, Santoni J P. The effect of perindopril and hydrochlorothiazide alone and in combination on blood pressure and on the renin-angiotensin system in hypertensive subjects. *Eur Clin Pharmacol* 1990; 39:327-32
37. Chrysant S G, Fagan T, Glazer R, Kriegman A. Effects of benazepril and hydrochlorothiazide, given alone and in low- and high-dose combinations, on blood pressure in patients with hypertension. *Arch Fam Med* 1996; 5:17-24
38. Frishman W H, Burris J F, Mroczek W J, Weir M R, Alemayehu D, Simon J S, et al. First-line therapy option with low-dose bisoprolol fumarate and low-dose hydrochlorothiazide in patients with stage I and stage II systemic hypertension. *J Clin Pharmacol* 1995; 35:182-8
39. Kayanakis J G, Baulac L. Comparative study of once-daily administration of captopril 50 mg, hydrochlorothi- 40. Moser M, Abraham P A, Bennett W M, Brachfeld N, Goodman R P, McKenney J M, et al. The effects of benazepril, a new angiotensin-converting enzyme inhibitor, in mild to moderate essential hypertension: a multicenter study. *Clin Pharmacol Ther* 1991; 49:322-9
41. Persson B, Stimpel M. Evaluation of the antihypertensive efficacy and tolerability of moexipril, an new ACE inhibitor, compared to hydrochlorothiazide in elderly patients. *Eur J Clin Pharmacol* 1996; 50:259-64
42. Jueng C, Halperin A K, Hasmimoto F, Callender K. Nifedipine GITS and hydrochlorothiazide in essential hypertension. *J Clin Hypertens* 1987; 3:695-703
43. Scholz D, Schwille P O, Sigel A. Double-blind study with thiazide in recurrent calcium lithiasis. *J Urol* 1982; 128:903-7
44. Materson B J, Oster J R, Michael U F, Bolton S M, Burton Z C, Stambaugh J E, et al. Dose response to chlorthalidone in patients with mild hypertension. *Clin Pharmacol Ther* 1978; 24:192-8
45. Morledge J H, Ettinger B, Aranda J, BcBarron F, Barra P, Gorwit J, et al. Isolated systolic hypertension in the elderly. A placebo-controlled, dose-response evaluation of chlorthalidone. *J Am Geriatr Soc* 1986; 34:199-206
46. Bateman D N, Dean C R, Mucklow J C, Bulpitt C J, Dollery C T. Atenolol and chlorthalidone in combination for hypertension. *Br J Clin Pharmacol* 1979; 7:357-63
47. Erwteman T M, Nagelkerke N, Lubsen J, Koster M, Dunning A J. β Blockade, diuretics, and salt restriction for the management of mild hypertension: a randomised double blind trial. *BMJ* 1984; 289:406-9
48. Ferrara L A, de Simone G, Mancini M, Fasano M L, Pasanisi F, Vallone G. Changes in left ventricular mass during a double-blind study with chlorthalidone and slow-release nifedipine. *Eur J Clin Pharmacol* 1984; 27:525-8
49. McFate Smith W M, Feigal D W, Furberg C D, Greenlick M, Kuller L, Perry H M, et al. Use of diuretics in treatment of hypertension in the elderly. *Drugs* 1986; 31:154-64
50. Moser M. Low-dose diuretic therapy for hypertension. *Clin Ther* 1986; 8:554-62
51. Salvetti A, Magagna A, Innocenti P, Ponzanelli F, Cagianelli A, Cipriani M, et al. The combination of chlorthalidone with nifedipine does not exert an additive antihypertensive effect in essential hypertensives: a crossover multicenter study. *J Cardiovasc Pharmacol* 1991; 17:332-5
52. Wing L M H, West M J, Graham J R, Chalmers J P. Long-acting and short-acting diuretics in mild essential hypertension. *Clin Exp Hypertens* 1982; A4:1429-41
53. Bradley K, Flack J M, Belcher J, Elmer P, Miller P, Grimm R. Chlorthalidone attenuates the reduction in total cholesterol and small, dense LDL cholesterol subclass associated with weight loss. *Am J Hypertens* 1993; 6:636-9
54. Cranston W I, Juel-Jensen B E. The effects of spironolactone and chlorthalidone on arterial pressure. *Lancet* 1962; 1:1161-4
55. Durel L A, Hayashi P J, Weidler D J, Schneiderman N. Effectiveness of antihypertensive medications in office and ambulatory settings: a placebo-controlled comparison of atenolol, metoprolol, chlorthalidone, verapamil, and an atenolol-chlorthalidone combination. *J Clin Pharmacol* 1992; 32:564-70
56. Hall W D, Weber M A, Ferdinand K, Flamenbaum W, Marbury T, Jain A K, et al. Lower dose diuretic therapy in the treatment of patients with mild to moderate hypertension. *J Hum Hypertens* 1994; 8:571-5
57. Fiddes R, Blumenthal J, Dawson J E, Dyckman E, Hammond P G S, Harris S, et al. Evaluation of indapamide 1.25 mg once daily in elderly patients with mild to moderate hypertension. *J Hum Hypertens* 1997; 11:239-44
58. Weidler D, Jallad N S, Curry C, Ferdinand K, Jain A K, Schnaper H W, et al. Efficacious response with lower dose indapamide therapy in the treatment of elderly patients with mild to moderate hypertension. *J Clin Pharmacol* 1995; 35:45-51
59. Borghi L, Meschi T, Guerra A, Novarini A. Randomized prospective study of a nonthiazide diuretic, indapamide, in preventing calcium stone recurrences. *J Cardiovasc Pharmacol* 1993; 22 (Suppl 6):S78-S86
60. Chalmers J P, Wing L M H, Grygiel J J, West M J, Graham J R, Bune A J. Effects of once daily indapamide and pindolol on blood pressure, plasma aldosterone concentration and plasma renin activity in a general practice setting. *Eur J Clin Pharmacol* 1982; 22:191-6
61. Schaller M, Waeber B, Brunner H R. Double-blind comparison of indapamide with a placebo in hypertensive patients treated by practicing physicians. *Clin Exp Hypertens* 1985; A7:985-94
62. Taylor D R, Constable J, Sonnekus M, Milne F J. Effect of indapamide on serum and red cell cations, with and without magnesium supplementation, in subjects with mild hypertension. *S Afr Med J* 1988; 74:272-6
63. Carlsen J E, Køber L, Torp-Pedersen, Johansen P. Relation between dose of bendrofluazide, antihypertensive effect, and adverse biochemical effects. *BMJ* 1990; 300:975-8
64. Christiansen C, Christensen M S, Hagen C, Stocklund K E, Transbøl. Effects of natural estrogen/gestagen and thiazide on coronary risk factors in normal postmenopausal women. *Acta Obstet Gynecol Scand* 1981; 60:407-412
65. Horvath J S, Caterson R J, Collett P, Duggin G G, Kelly D H, Tiller D J. Labetalol and bendrofluazide: comparison of their antihypertensive effects. *Med J Aust* 1979; 1:626-8
66. Webster J, Dollery C T, Hensby C N. Circulating prostacyclin concentrations may be increased by bendrofluazide in patients with essential hypertension. *Clin Sci* 1980; 59 (Suppl 6):125s-128s
67. Wilcox R G. Randomised study of six beta-blockers and a thiazide diuretic in essential hypertension. *BMJ* 1978; 2:383-5
68. Fernandez P G, Zachariah P K, Bryant D G, Missan S S. Antihypertensive efficacy of α-methyldopa, chlorothiazide and Supres-150 α-methyldopa-chlorothiazide). *Can Med Assoc J* 1980; 123:284-7
69. Curry C L, Harris R, MacKay J H, Nugent C A, Ryan J, Schnaper, et al. Clinical studies of a new, low-dose formulation of metolazone for the treatment of hypertension. *Clin Ther* 1986; 9:47-62
70. McVeigh G, Galloway D, Johnston D. The case for low dose diuretics in hypertension: comparison of low and conventional doses of cyclopenthiazide. *BMJ* 1988; 297:95-8
71. Chrysant S G, Chappel C, Farnham J, Levin B, Lueg M, McCluskey D, et al. Antihypertensive and metabolic effects of single and combined atenolol regimens. *J Clin Pharmacol* 1992; 32:61-65

72. Ekbom T, Dahlöf B, Hansson L, Lindholm L H, Schersten B, Wester P. Antihypertensive efficacy and side effects of three beta-blockers and a diuretic in elderly hypertensives: a report from the STOP-Hypertension study. *J Hypertens* 1991; 10:1525-9
73. Gostick N K, Mayhew S R, Million R, Sagar D, Suxena S R, Igram D F, et al. A dose-response study of atenolol in mild to moderate hypertension in general practice. *Curr Med Res Opin* 1977; 5:179-84
74. Saul P, Jones B P, Edwards K G, Tweed J A. Randomized comparison of atenolol and placebo in the treatment of anxiety: a double-blind study. *Eur Clin Pharmacol* 1985; 28:109-110
75. Tonkin A L, Wing L M H, Russell A E, West M J, Bune A J C, Morris M J, et al. Diltiazem and atenolol in essential hypertension: additivity of effects on blood pressure and cardiac conduction with combination therapy. *J Hypertens* 1990; 8:1015-8
76. Wing L M H, Chalmers J P, West M J, Russell A E, Morris M J, Cain M D. Enalapril and atenolol in essential hypertension: attenuation of hypertensive effects in combination. *Clin Exp Hypertens* 1988; 10:119-33
77. Cilliers A J. Atenolol as primary therapy in previously untreated hypertensives and as an adjuvant to other therapy. *S Afr Med J* 1979; 55:321-4
78. Clement D L, De Pue N Y, Packet L. Effect of calcium antagonists on ambulatory blood pressure and its variations. *J Cardiovasc Pharmacol* 1987; 10 (Suppl 10):5117-5119
79. Houston M C, Burger C, Hays J T, Nadeau J, Swift L, Bradley C A, et al. The effects of clonidine hydrochloride versus atenolol monotherapy on serum lipids, lipid subfractions, and apolipoproteins in mild hypertension. *Am Heart J* 1990; 120:172-9
80. Lange-Andersen K L, Ottmann W, Piatkowski W, Green K A. Working ability and exercise tolerance during treatment of mild hypertension. *Int Arch Occup Environ Health* 1985; 56:49-55
81. Lyons D, Fowler G, Webster J, Hall S T, Petrie J C. An assessment of lacidipine and atenolol in mild to moderate hypertension. *Br J Clin Pharmacol* 1994; 37:45-51
82. Streufert S, DePadova A, McGlynn T, Pogash R, Piasecki M. Impact of β-blockade on complex cognitive functioning. *Am Heart J* 1988; 116:311-4
83. Tötterman K, Groop L, Groop P, Kala R, Tolppanen, Fyhrquist F. Effect of beta-blocking drugs on beta-cell function and insulin sensitivity in hypertensive non-diabetic patients. *Eur J Clin Pharmacol* 1984; 26:13-7
84. Vanhees L, Fagard R, Lijnen P, Amery A. Effect of antihypertensive medication on endurance exercise capacity in hypertensive sportsmen. *J Hypertens* 1991; 9:1063-8
85. Verdecchia P, Gatteschi C, Benemio G, Boldrini F, Guerrieri M, Porcellati C. Duration of the antihypertensive action of atenolol, enalapril and placebo. *Int J Clin Pharmacol Ther Toxicol* 1988; 26:570-4
86. Clement D L, Bogaert M G, Pannier R. Effect of beta-adrenergic blockage on blood pressure variation in patients with moderate hypertension. *Eur J Clin Pharmacol* 1977; 11:325-7
87. Baez M A, Garg D C, Jallad N S, Weidler D J. Antihypertensive effect of doxazosin in hypertensive patients: comparison with atenolol. *Br J Clin Pharmacol* 1986; 21 (Suppl 1):63S-67S
88. Jeffers T A, Webster J, Petrie J C. Atenolol once-daily in hypertension. *Br J Clin Pharmacol* 1977; 4:523-7
89. Maclean D, Mitchell E T, Lewis R, Irvine N, McLay S, McEwen J, et al. Comparison of once daily atenolol, nitrendipine and their combination in mild to moderate essential hypertension. *Br J Clin Pharmacol* 1990; 29:455-63
90. Van Nueten L, Taylor F R, Robertson J I S. Nebivolol vs atenolol and placebo in essential hypertension: a double-blind randomised trial. *J Hum Hypertens* 1998; 12:135-40
91. Petrie C, Jeffers T A, Robb O J, Scott A K, Webster J. Atenolol, sustained-release oxprenolol, and long-acting propranolol in hypertension. *BMJ* 1980; 1:1573-4
92. Wilcox R G, Hampton J R. Comparative study of atenolol, metoprolol, metoprolol durules, and slow-release oxprenolol in essential hypertension. *Br Heart J* 1981; 46:498-502
93. Roberts D H, Tsao Y, MCLoughlin G A, Breckenridge A. Placebo-controlled comparison of captopril, atenolol, labetalol, and pindolol in hypertension complicated by intermittent claudication. *Lancet* 1987; 2:650-3
94. Hansson L, Aberg H, Karlberg B E, Westerlund A. Controlled study of atenolol in treatment of hypertension. *BMJ* 1975; 2:367-70
95. Broekman C P M, Haensel S M, Ven de Ven L L M, Slob A K. Bisoprolol and hypertension: effects on sexual functioning in men. *J Sex Marital Ther* 1992; 18:325-31
96. Davidov M E, Singh S P, Vlachakis N D, Blumenthal J B, Simon J S, Bryzinski J S, et al. Bisoprolol, a once-a-day beta-blocking agent for patients with mild to moderate hypertension. *Clin Cardiol* 1994; 17:263-268
97. Tseng C, Chiang F, Hsu K, Tseng Y, Hu W, Chen J, et al. Short-term efficacy and safety of bisoprolol in treatment of patients with mild-to-moderate hypertension—A two-center, double-blind study in Taiwan. *Acta Cardiologica Sinica* 1993; 9:155-60
98. Van de Ven L L M, Mouthaan B J, Hoes M J. Treatment of hyperventilation syndrome with bisoprolol: a placebo-controlled clinical trial. *J Psychosom Res* 1995; 39:1007-13
99. Asmar R G, Kerihuel J C, Girerd X J, Safar M E. Effect of bisoprolol on blood pressure and arterial hemodynamics in systemic hypertension. *Am J Cardiol* 1991; 68:61-4
100. Ameling E H, de Korte D F, Man in 't Veld A J. Impact of diagnosis and treatment of hypertension on quality of life: a double-blind, randomized, placebo-controlled, cross-over study of betaxolol. *J Cardiovasc Pharmacol* 1991; 18:752-60
101. Williams R L, Goyle K K, Herman T S, Rofman B A, Ruoff G E, Hogan L B. Dose-dependent effects of betaxolol in hypertension: a double-blind multicenter study. *J Clin Pharmacol* 1992; 32:360-7
102. Salonen J T, Palminteri R. Comparison of two doses of betaxolol and placebo in hypertension: a randomised, double-blind cross-over trial. *Eur J Clin Pharmacol* 1982; 23:491-4
103. Jäättelä A, Baandrup S, Houtzagers J, Westergren G. The efficacy of low dose metoprolol CR/ZOK in mild hypertension and in elderly patients with mild to moderate hypertension. *J Clin Pharmacol* 1990; 30 (Suppl):S66-S71
104. Landin K, Tengborn L, Smith U. Metformin and metoprolol CR treatment in non-obese men. *J Intern Med* 1994; 235:335-41
105. Groop L, Tötterman K J, Harno K, Gordin A. Influence of beta-blocking drugs on glucose metabolism in hypertensive, non-diabetic patients. *Acta Med Scand* 1983; 213:9-14

106. Lepäntalo M J A, Tötterman K J. Lower limb haemodynamics during antihypertensive treatment with metoprolol and propranolol. *Inter Angiol* 1985; 4:225-8

107. MacMahon S, MacDonald G J, Bernstein L, Andrews G, Blacket R B. Comparison of weight reduction with metoprolol in treatment of hypertension in young overweight patients. *Lancet* 1985; 1:1233-6

108. Reybrouck T, Amery A, Fagard R, Jousten P, Lijnen P, Meulepas E. Beta-blockers: once or three times a day? *BMJ* 1978; 1:1386-8

109. Vandongen R, Margetts B, Deklerk N, Beilin L J, Rogers P. Plasma catecholamines following exercise in hypertensives treated with pindolol: comparison with placebo and metoprolol. *Br J Clin Pharmacol* 1986; 21:627-32

110. Trafford J A P, Latta D, Little P S, Parsley J, Ankier S I. A multi-centre, placebo controlled comparative study between 200 mg and 400 mg celiprolol in patients with mild to moderate essential hypertension. *Curr Med Res Opin* 1989; 11:550-6

111. Kimura S, DeQuattro V, Hernandez P H, Lee D D. Effects of celiprolol on plasma renin, aldosterone, norepinephrine and epinephrine in primary hypertension. *Am J Cardiol* 1988; 62:751-4

112. Watson R D S, Stallard T J, Littler W A. Comparison of once and twice daily administration of acebutolol in hypertension. *Br J Clin Pharmacol* 1980; 9:209-12

113. Van Nueten L, Dupont A G, Vertommen C, Goyvaerts H, Robertson J I S. A dose-response trial of nebivolol in essential hypertension. *J Hum Hypertens* 1997; 11:139-44 Himmelmann A, Hedner T, Ssnoeck E, Lundgren B, Hedner J. Haemodynamic effects and pharmacokinetics of oral d- and l-nebivolol in hypertensive patients. *Eur J Clin Pharmacol* 1996; 51:259-64

115. Glassock R J, Weitzman R E, Bennett C M, Maxwell M, Hamilton B, Winer N, et al. Pindolol: effects on blood pressure and plasma renin activity. *Am Heart J* 1982; 104:421-5

116. Hamilton B P, Hamilton J, Kirkendall W M. Pulmonary function in hypertensive patients treated with pindolol: a report of two studies. *Am Heart J* 1982; 104:432-7

117. Galloway D B, Glover S C, Hendry W G, Logie A W, Petrie J C, Smith M C, et al. Propranolol in hypertension: a dose-response study. *BMJ* 1976; 2:140-2

118. Dargie H, Cleland J, Findlay I, Murray G, McInnes G. Combination of verapamil and beta-blockers in systemic hypertension. *Am J Cardiol* 1986; 57:80 D-82D 119. McInnes G T, Findlay I N, Murray G, Cleland J G F, Dargie H J. Cardiovascular responses to verapamil and propranolol in hypertensive patients. *J Hypertens* 1985; 3 (Suppl 3):5219-21

120. Hudson C F E. An evaluation of once daily long acting propranolol hydrochloride (Inderal L A and Half-Inderal L A) in the treatment of anxiety. A double-blind placebo-controlled general practice study. *Br J Clin Pract* 1988; 42:419-26

121. Pearson R M, Bulpitt C J, Havard C W H. Biochemical and haematological changes induced by tienilic acid combined with propranolol in essential hypertension. *Lancet* 1979; 1:697-9

122. Moleur P, Peyrieux J C, Luciani J, David D, Boissel J P. Bopindolol in the treatment of moderate hypertension: a dose-response study. *Fundam Clin Pharmacol* 1988; 2:431-40

123. Adsett C A, Bellissimo A, Mitchell A, Wilczynski N, Haynes R B. Behavioral and physiological effects of a beta-blocker and relaxation therapy on mild hypertensives. *Psychosom Med* 1989; 51:523-6

124. Dupont A G, Vanderniepen P, Bossuyt A M, Jonckheer M H, Six R O. Nadolol in essential hypertension: effect on ambulatory blood pressure, renal haemodynamics and cardiac function. *Br J Clin Pharmacol* 1985; 20:93-99

125. Casadei B, Conway J, Coats A J S, Bird R. Antihypertensive effect of carvedilol: a preliminary dose-response study. *Clinical Investigigator* 1992; 70 (Suppl): S37-S38

126. Dupont A G, Van der Niepen P, Taeymans Y, Ingels M, Piepsz A, Bossuyt A M, et al. Effect of carvedilol on ambulatory blood pressure, renal hemodynamics, and cardiac function in essential hypertension. *J Cardiovasc Pharmacol* 1987; 10 (Suppl 11):S130-S136

127. Morgan T O, Morgan O, Anderson A. Effect of dose on trough peak ratio of antihypertensive drugs in elderly hypertensive males. *Clin Exp Pharmacol Physiol* 1995; 22:778-80

128. Chrysant S G, Brown R D, Kem D C, Brown J L. Antihypertensive and metabolic effects of a new converting enzyme inhibitor, enalapril. *Clin Pharmacol Ther* 1983; 33:741-6

129. Kaski J C, Rosano G, Gavrielides S, Chen L. Effects of angiotensin-converting enzyme inhibition on exercise induced angina and ST segment depression in patients with microvascular angina. *J Am Coll Cardiol* 1987; 23:652-7

130. Küppers H E, Jäger B A, Luszick J H, Grave, Hughes P R, Kaan E C. Placebo-controlled comparison of the efficacy and tolerability of once-daily moxonidine and enalapril in mild-to-moderate essential hypertension. *J Hypertens* 1997; 15:93-7

131. Naranjo C A, Kadlec K E, Sanhueza P, Woodley-Remus D, Sellers E M. Enalapril effects on alcohol intake and other consummatory behaviors in alcoholics. *Clin Pharmacol Ther* 1991; 50:96-106

132. Simon G, Morioka S, Snyder D K, Cohn J N. Increased renal plasma flow in long-term enalapril treatment of hypertension. *Clin Pharmacol Ther* 1983; 34:459-65

133. van Baak M A, Mooij J M V, Wijnen J A G, Tan F S. Submaximal endurance exercise performance during enalapril treatment in patients with essential hypertension. *Clin Pharmacol Ther* 1991; 50:221-7

134. Whelton A, Dunne B, Glazer N, Kostis J B, Miller W E, Rector D J, et al. Twenty-four hour blood pressure effect of once-daily lisinopril, enalapril, and placebo in patients with mild to moderate hypertension. *J Hum Hypertens* 1992; 6:325-31

135. Gibbs J S R, Crean P A, Mockus L, Wright C, Sutton G, Fox K M. The variable effects of angiotensin converting enzyme inhibition on myocardial ischaemia in chronic stable angina. *Br Heart J* 1989; 62:112-7

136. Gradman A H, Arcuri K E, Goldberg A I, Ikeda L S, Nelson E B, Snavely D B, et al. A randomized, placebo-controlled, double-blind, parallel study of various doses of losartan potassium compared with enalapril maleate in patients with essential hypertension. *Hypertension* 1995; 25:1345-50

137. Krum H, Viskoper R J, Lacourciere Y, Budde M, Charlon V. The effect of an endothelin-receptor antagonist, bosentan, on blood pressure in patients with essential hypertension. *N Eng J Med* 1998; 338:784-90

138. Forette F, Handfield-Jones R, Henry-Amar M, Fouchard M, Bouchacourt P, Hervy M, et al. Rationale for ACE inhibition in the elderly: treatment of arterial hypertension with enalapril. *Gerontology* 1987; 33:9-16 Sassano P, Chatellier G, Alhenc-Gelas F, Corvol P, Menard J.

Antihypertensive effect of enalapril as first-step treatment of mild and moderate uncomplicated essential hypertension. *Am J Med* 1984; 77(suppl 2A): 18-22

140. Applegate W B, Cohen J D, Wolfson P, Davis A, Green S. Evaluation of blood pressure response to the combination of enalapril (single dose) and diltiazem ER (four different doses) in systemic hypertension. *Am J Cardiol* 1996; 78:51-5

141. Cushman W C, Cohen J D, Jones R P, Marbury T C, Rhoades R B, Smith L K. Comparison of the fixed combination of enalapril/diltiazem ER and their monotherapies in stage 1 to 3 essential hypertension. *Am J Hypertens* 1998; 11:23-30

142. Franke H. Antihypertensive effects of candesartan cilexetil, enalapril and placebo. *J Hum Hypertens* 1997; 11 (Suppl 2):561-62

143. Levine J H, Ferdinand K C, Cargo P, Laine H, Lefkowitz M. Additive effects of verapamil and enalapril in the treatment of mild to moderate hypertension. *Am J Hypertens* 1995; 8:494-9

144. Salvetti A, Arzilli F. Chronic dose-response curve of enalapril in essential hypertensives. *Am J Hypertens* 1989; 2:352-4

145. Holwerda N J, Fogari R, Angeli P, Porcellati C, Hereng C, Oddou-Stock P, et al. Valsartan, a new angiotensin II antagonist for the treatment of essential hypertension: efficacy and safety compared with placebo and enalapril. *J Hypertens* 1996; 14:1147-51

146. Bergstrand R, Herlitz H, Johansson S, Berglund G, Vedin A, Wilhelmsson C, et al. Effective dose range of enalapril in mild to moderate essential hypertension. *Br J Clin Pharmacol* 1985; 19:605-11

147. Louis W J, Workman B S, Conway E L, Worland P, Rowley K, Drummer O, et al. Single-dose and steady-state pharmacokinetics and pharmacodynamics of perindopril in hypertensive subjects. *J Cardiovasc Pharmacol* 1992; 20:505-11

148. Luccioni R, Frances Y, Gass R, Gilgenkrantz J M. Evaluation of the dose-effect relationship of perindopril in the treatment of hypertension. *Clin Exp Hypertens* 1989; A11:521-34

149. Myers M G. A dose-response study of perindopril in hypertension: effects on blood pressure 6 and 24 h after dosing. *Am J Cardiol* 1996; 12:1191-6

150. West J N R, Smith S A, Stallard T J, Littler W A. Effects of perindopril on ambulatory intra-arterial blood pressure, cardiovascular reflexes and forearm blood flow in essential hypertension. *J Hypertens* 1989; 7:97-104

151. Chrysant S G, McDonald R H, Wright J T, Barden P L, Weiss R J. Perindopril as monotherapy in hypertension: a multicenter comparison of two dosing regimens. *Clin Pharmacol Ther* 1993; 53:479-84

152. Overlack A, Adamczak M, Bachmann W, Bonner G, Bretzel R G, Derichs R, et al. ACE-inhibition with perindopril in essential hypertensive patients with concomitant diseases. *Am J Med* 1994; 97:126-34

153. Veterans Administration Cooperative Study Group on Antihypertensive Agents. Low-dose captopril for the treatment of mild to moderate hypertension. *Arch Intern Med* 1984; 144:1947-53

154. Drayer J I M, Weber M A. Monotherapy of essential hypertension with a converting-enzyme inhibitor. *Hypertens* 1983; 5 (Suppl III): 111108-13

155. Schoenberger J A, Wilson D J. Once-daily treatment of essential hypertension with captopril. *J Clin Hypertens* 1986; 4:379-87

156. Conway J, Way B, Boon N, Somers V. Is the antihypertensive effect of captopril influenced by the dosage frequency? A study with ambulatory monitoring. *J Hum Hypertens* 1988; 2:123-6

157. Lavessaro G, Ladetto P E, Valente M, Stramignoni D, Zanna C, Assogna G, et al. Ketanserin and captopril interaction in the treatment of essential hypertensives. *Cardiovasc Drugs Ther* 1990; 4:119-22

158. Salvetti A, Innocenti P F, Iardella M, Pambianco F, Saba G C, Rossetti M, et al. Captopril and nifedipine interactions in the treatment of essential hypertensives: a crossover study. *J Hypertens* 1987; 5 (Suppl 4):5139-5142

159. Salvetti A, Circo A, Raciti S, Gulizia M, Cardillo R, Miceli S, et al. Captopril at 50 mg as well as at 100 mg once a day reduces blood pressure for up to 24 h: a double-blind randomized crossover study in mild to moderate hypertensives. *J Hypertens* 1988; 6 (Suppl 4):5666-5668

160. Fernandez P G, Bolli P, Lee C. The 24 h blood pressure responses of hypertensives to a once-a-day cilazapril regimen. *Can J Cardiol* 1990; 6:53-8

161. Guntzel P, Kobrin I, Pasquier C, Zimlichman R, Viskoper J R. The effect of cilazapril, a new angiotensin converting enzyme inhibitor, on peak and trough blood pressure measurements in hypertensive patients. *J Cardiovasc Pharmacol* 1991; 17:8-12

162. Kobrin I, Guntzel P, Viskoper R, Paran E, Zimlichman R. Antihypertensive duration of action of cilazapril in patients with mild to moderate essential hypertension. *Drugs* 1991; 41:31-6

163. Krum H, Jackson B, Conway E L, Howes L G, Johnston C I, Louis W J. Steady-state pharmacokinetics and pharmacodynamics of cilazapril in the presence and absence of cyclopenthiazide. *J Cardiovasc Pharmacol* 1992; 20:451-7

164. Lacourcière Y, Leenen F, Rangno R, Spence J D, Lenis J H, Myers M G. Discrepancies between clinic and ambulatory blood pressure responses to cilazapril therapy. *Can J Cardiol* 1994; 10:605-10

165. Mroczek W J, Klein J, Burris J F. Dose-finding study of cilazapril (inhibace) in patients with uncomplicated essential hypertension. *Clin Exp Hypertens* 1991; A13: 1415-32

166. Prager G, Klein P, Schmitt M, Prager R. Antihypertensive efficacy of cilazapril 2.5 and 5.0 mg once-daily versus placebo on office blood pressure and 24-hour blood pressure profile. *J Cardiovasc Pharmacol* 1994; 24 (Suppl 3):593-S99

167. White W B, McCabe E J, Hager W D, Schulman P. The effects of the long-acting angiotensin-converting enzyme inhibitor cilazapril on casual, exercise and ambulatory blood pressure. *Clin Pharmacol Ther* 1988; 44 (Suppl 3):173-8

168. Poirier L, Pyzyk M, Provencher P, Lacourciére. Comparative effects of 2.5 and 5 mg cilazapril versus placebo on daily blood pressure load. *Am J Hypertens* 1991; 4:913-5

169. DeQuattro V, Lee D. Fixed-dose combination therapy with trandolapril and verapamil SR is effective in primary hypertension. *Am J Hypertens* 1997; 10 (Suppl):1385-1455

170. Veratran Study Group. Effects of verapamil SR, trandolapril, and their fixed combination on 24-h blood pressure. *Am J Hypertens* 1997; 10:492-9

171. Weir M R, Gray J M, Paster R, Saunders E. Differing mechanisms of action of angiotensin-converting enzyme 171. inhibition in black and white hypertensive patients. *Hypertension* 1995; 26:124-30
172. Mancia G, De Cesaris R, Fogari R, Lattuada S, Montemurro G, Palombo C, et al. Evaluation of the antihypertensive effect of once-a-day trandolapril by 24-hour ambulatory blood pressure. *Am J Cardiol* 1992; 70:60 D-66D
173. De Bruijn J H B, Orofiamma B A, Pauly N C. Efficacy and tolerance of trandolapril (0.5-2 mg) administered for 4 weeks in patients with mild-to-moderate hypertension. *J Cardiovasc Pharmacol* 1994; 23 (Suppl 4):560-S64
174. Messerli F, Frishman W H, Elliott W J. Effects of verapamil and trandolapril in the treatment of hypertension. *Am J Hypertens* 1998; 11:322-7
175. Ford N F, Fulmor T E, Nichola P S, Alpin P G, Herron J M. Fosinopril monotherapy: relationship between blood pressure reduction and time of administration. *Clin Cardiol* 1993; 16:324-30
176. Pool J L. Antihypertensive effect of fosinopril, a new angiotensin converting enzyme inhibitor: findings of the Fosinopril Study Group II. *Clin Ther* 1990; 12:520-33
177. Anderson R J, Duchin K L, Gore R D, Herman T S, Michaels R S, Nichola P S, et al. Once-daily fosinopril in the treatment of hypertension. *Hypertension* 1991; 17:636-42
178. Maclean D. Quinapril: a double-blind, placebo-controlled trial in essential hypertension. *Angiology* 1989; 40:370-81
179. Säynävälammi P, Pörsti I, Pörsti P, Nurmi A, Seppälä E, Manninen V, et al. Effects of the converting enzyme inhibitor quinapril on blood pressure, renin-angiotensin system and prostanoids in essential hypertension. *J Cardiovasc Pharmacol* 1988; 12:88-93
180. Gupta R K, Kjeldsen S E, Motley E, Weder A B, Sweifler A J, Julius S. Platelet function during antihypertensive treatment with quinapril, a novel angiotensin converting enzyme inhibitor. *J Cardiovasc Pharmacol* 1991; 17:13-9
181. Kjeldsen S E, Gupta R K, Krause L, Weder A B, Julius S. Does blood pressure reduction necessarily compromise cardiac function or renal hemodynamics? Effects of the angiotensin-converting enzyme inhibitor quinapril. *Am Heart J* 1992; 123:1433-8
182. Black H R, Graff A, Shute D, Stoltz R, Ruff D, Levine J, et al. Valsartan, a new angiotensin II antagonist for the treatment of essential hypertension: efficacy, tolerability and safety compared to an angiotensin-converting enzyme inhibitor, lisinopril. *J Hum Hypertens* 1997; 11:483-9
183. Paolisso G, Balbi V, Gambardella A, Varricchio G, Tortoriello R, Saccomanno F, et al. Lisinopril administration improves insulin action in aged patients with hypertension. *J Hum Hypertens* 1995; 9:541-6
184. Thürig C, Böhlen L, Schneider M, de Courten M, Shaw S G, Riesen W, et al. Lisinopril is neutral to insulin sensitivity and serum lipoproteins in essential hypertensive patients. *Eur J Clin Pharmacol* 1995; 49:21-6
185. Tomei R, Rossi L, Carbonieri E, Franceschini L, Molon G, Zardini P. Antihypertensive effect of lisinopril assessed by 24-hour ambulatory monitoring: a double-blind, placebo-controlled, cross-over study. *J Cardiovasc Pharmacol* 1992; 19:911-14
186. Polónia J, Martins L, Macedo F, Faria D B, Simões, Brandão F, et al. Lisinopril and diltiazem reduce left ventricular mass without changing blood pressure in normotensive subjects with exaggerated blood pressure response to exercise. *Rev Port Cardiol* 1996; 15:185-93
187. Gomez J H, Cirillo V J, Sromovsky J A, Otterbein E S, Shaw W C, Rush J E, et al. Lisinopril dose-response relationship in essential hypertension. *Br J Clin Pharmacol* 1989; 28:415-20
188. Chan P, Lin C, Tomlinson B, Lin T, Lee Y. Additive effects of diltiazem and lisinopril in treatment of elderly patients with mild-to-moderate hypertension. *Am J Hypertens* 1997; 10:743-9
189. Burris J F. The effect of ramipril on ambulatory blood pressure: a multicenter study. *J Cardiovasc Pharmacol* 1991; 18 (Suppl 2): S131-3
190. McCarron D. 24-hour blood pressure profiles in hypertensive patients administered ramipril or placebo once daily: magnitude and duration of antihypertensive effects. *Clin Cardiol* 1991; 14:737-42
191. Schnaper H W. Dose-response relationship of ramipril in patients with mild-to-moderate hypertension. *J Cardiovasc Pharmacol* 1991; 18 (Suppl 2): S128-S130
192. Homuth V, Faulhaber H, Loose U, Löffler K, Luft F C. Usefulness of piretanide plus ramipril for systemic hypertension: a multicenter trial. *Am Cardiol* 1993; 72:666-71
193. Villamil A S, Cairns V, Witte P U, Bertolasi C A. A double-blind study to compare the efficacy, tolerance and safety of two doses of the angiotensin converting enzyme inhibitor ramipril with placebo. *Am J Cardiol* 1987; 59:110 D-114D
194. Guitard C, Lohmann F W, Alfiero R, Ruina M, Alvisi V. Comparison of efficacy of spirapril and enalapril in control of mild-to-moderate hypertension. *Cardiovasc Drugs Ther* 1997; 11:449-57
195. Guitard C, Sasssano P, Tzincoca C, Duchiez J, Safar M E. Placebo-controlled crossover comparison of spirapril at 3, 6, 12 and 24 mg once daily in mild to severe essential hypertension. *Blood Press* 1994; 3 (suppl 2):61-8
196. Guitard C, Alvisi V, Maibach E, Franck J, Cocco G, Boxho G, et al. Placebo-controlled comparison of spirapril at 6, 12 and 24 mg/day in mild to severe essential hypertension. *Blood Press* 1994; 3 (suppl 2):81-7
197. Fairhurst G J. A multicentre multidose study of the efficacy and safety of spirapril in mild-to-moderate essential hypertension. *Blood Press* 1994; 3 (suppl 2):77-80
198. Frishman W H, Ram C V S, McMahon F G, Chrysant S G, Graff A, Kupiec J W, et al. Comparison of amlodipine and benazepril monootherapy to amlodipine plus benazepril in patients with systemic hypertension: a randomized, double-blind, placebo-controlled, parallel-group study. *J Clin Pharmacol* 1995; 35:1060-6
199. Kuschnir E, Acuña E, Sevilla D, Vasquez J, Bendersky M, Resk J, et al. Treatment of patients with essential hypertension: amlodipine 5 mg/benazepril 10 mg compared with amlodipine 5 mg, benazepril 20 mg, and placebo. *Clin Ther* 1996; 18:1213-24
200. Nawrocki J W, Weiss S R, Davidson M H, Sprecher D L, Schwartz S L, Lupien P-J, et al. Reduction of LDL cholesterol by 25% to 60% in patients with primary hypercholesterolemia by atorvastatin, a new HMG-CoA reductase inhibitor. *Arterioscler Thromb Vasc Biol* 1995; 15:678-82
201. Wald N J, Law M R. Serum cholesterol and ischaemic heart disease. *Atherosclerosis* 1995; 118 (Suppl): 51-5.
202. Crouse J R, Byington R P, Furberg C D. HMG-CoA reductase inhibitor therapy and stroke risk reduction: an analysis of clinical trials data. *Atherosclerosis* 1998B138: 11-24
203. Boysen G, Sørensen S, Juhler M, Andersen A R, Boas J, Oslen J S, et al. Danish very-low dose aspirin after carotid endarterectomy trial. *Stroke* 1988; 19:1211-15

204. Sivenius J, Cunha L, Diener H-C, Forbes C, Laakso M, Lowenthal, et al. Second European stroke prevention study: antiplatelet therapy is effective regardless of age. *Act Neurol Scand* 1999; 99:54-60
205. Juul-Möller S, Edvardsson N, Jahnmatz B, Rosén A, Sørensen S, Ömblus R, et al. Double-blind trial of aspirin in primary prevention of myocardial infarction in patients with stable chronic angina pectoris. *Lancet* 1992; 340: 1421-5
206. The Salt Collaborative Group. Swedish aspirin low-dose trial (SALT) of 75 mg aspirin as secondary prophylaxis after cerebrovascular ischaemic events. *Lancet* 1991; 338:1345-9
207. Nyman I, Larsson H, Wallentin L, and The Research Group on Instability in Coronary Artery Disease in Southeast Sweden. Prevention of serious cardiac events by low-dose aspirin in patients with silent myocardial ischaemia. *Lancet* 1992; 340:497-501
208. The RISC Group. Risk of myocardial infarction and death during treatment with low dose aspirin and intravenous heparin in men with unstable coronary artery disease. *Lancet* 1990; 336:827-30
209. Petersen P, Boysen G, Godtfredsen J, Andersen E D, Andersen B. Placebo-controlled, randomised trial of warfarin and aspirin for prevention of thromboembolic complications in chronic atrial fibrillation. *Lancet* 1989; 1:175-9
210. Wallentin L C, The Research Group on Instability in Coronary Artery Disease in Southeast Sweden. Aspirin (75 mg/day) after an episode of unstable coronary artery disease: long-term effects on the risk for myocardial infarction, occurrence of severe angina and the need for revascularization. *J Am Coll Cardiol* 1991; 18:1587-93
211. Yasue H, Ogawa H, Tanaka H, Miyazaki S, Hattori R, Saito M, et al. Effects of aspirin and trapidil on cardiovascular events after acute myocardial infarction. *Am J Cardiol* 1999; 83:1308-13
212. Posada I S, Barriales V. Alternate-day dosing of aspirin in atrial fibrillation. *Am Heart J* 1999; 138:137-43
213. Meister W, v Schacky C, Weber M, Lorenz R, Kotzur J, Reichart B, et al. Low-dose acetylsalicylic acid (100 mg/day) after aortocoronary bypass surgery: a placebo-controlled trial. *Br J Clin Pharmac* 1984:17:703-11
214. The Medical Research Council's General Practice Research Framework. Thrombosis prevention trial: a randomised trial of low-intensity oral anticoagulation with warfarin and low-dose aspirin in the primary prevention of ischaemic heart disease in men at increased risk. *Lancet* 1998; 351:233-41
215. Hansson L, Zanchetti A, Carruthers S G, Dahlöf B, Elmfeldt D, Julius S, et al. Effects of intensive blood-pressure and low-dose aspirin in patients with hypertension: principal results of the Hypertension Optimal Treatment (HOT) randomised trial. *Lancet* 1998; 351:1755-62
216. Silagy C A, McNeil J J, Donnan G A, Tonkin A M, Worsam B, Campion K. Adverse effects of low-dose aspirin in a healthy elderly population. *Clin Pharmacol Ther* 1993; 54:84-9
217. Homocysteine Lowering Trialist's Collaboration. Lowering blood homocysteine with folic acid based supplements: meta-analysis of randomised trials. *BMJ* 1998; 316:894-8
218. Wald N J, Law M, Watt H C, Wu T, Bailey A, Johnson A M, et al. Apolipoproteins and ischaemic heart disease: implications for screening. *Lancet* 1994; 343:75-9

The invention claimed is:
1. A formulation comprising:
 (a) at least two drugs from the category of blood pressure lowering agents, each selected from a different physiological mode of action selected from a diuretic, a beta blocker, an angiotensin converting enzyme (ACE) inhibitor, an angiotensin II receptor antagonist, and a calcium channel blocker; and
 (b) drugs from at least two of the following three categories:
  i) at least one lipid-regulating agent,
  ii) at least one platelet function altering agent, and
  iii) at least one serum homocysteine lowering agent;
  wherein said formulation reduces the risk of cardiovascular disease.
2. A formulation according to claim 1, wherein the dose of each blood pressure lowering agent is below a recommended lower therapeutic dosage for the blood pressure lowering agent.
3. A formulation comprising
 (a) at least two drugs from the category of blood pressure lowering agents independently selected from a diuretic, a beta blocker, an angiotensin converting enzyme (ACE) inhibitor, an angiotensin II receptor antagonist, and a calcium channel blocker;
 (b) at least one lipid-regulating agent; and
 (c) optionally, drugs from at least one of the following two categories:
  i) at least one platelet function altering agent, and
  ii) at least one serum homocysteine lowering agent,
 wherein the dose of the blood pressure lowering agent is below a recommended lower therapeutic dosage for the blood pressure lowering agent; and wherein said formulation reduces the risk of cardiovascular disease.
4. A formulation, comprising:
 i) about 12.5 mg hydrochlorothiazide, about 25 mg atenolol, and about 5 mg enalapril as blood pressure lowering agents,
 ii) from about 10 mg atorvastatin as a lipid-regulating agent,
 iii) about 75 mg aspirin as a platelet function altering agent, and
 iv) about 0.8 mg folic acid as a serum homocysteine lowering agent;
 wherein each specified dose is the daily dose.
5. A formulation, comprising:
 i) about 12.5 mg hydrochlorothiazide, about 25 mg atenolol, and about 5 mg enalapril as blood pressure lowering agents,
 ii) about 20 mg simvastatin as a lipid-regulating agent,
 iii) about 75 mg aspirin as a platelet function altering agent, and
 iv) about 0.8 mg folic acid as a serum homocysteine lowering agent;
 wherein each specified dose is the daily dose.
6. The formulation of claim 1, wherein the dose of each blood pressure lowering agent is about half of the recommended lower therapeutic dosage for said blood pressure lowering agent.
7. The formulation of claim 2, wherein the dose of the blood pressure lowering agent is about half of the recommended lower therapeutic dosage for said blood pressure lowering agent.
8. The formulation of claim 3, wherein the dose of the blood pressure lowering agent is about half of the recommended lower therapeutic dosage for said blood pressure lowering agent.

9. A formulation, comprising:
i) about 12.5 mg hydrochlorothiazide, about 25 mg atenolol, and about 5 mg enalapril as blood pressure lowering agents,
ii) from about 10 mg atorvastatin as a lipid-regulating agent,
iii) about 0.8 mg folic acid as a serum homocysteine lowering agent;
wherein each specified dose is the daily dose.

10. A formulation, comprising:
i) about 12.5 mg hydrochlorothiazide, about 25 mg atenolol, and about 5 mg enalapril as blood pressure lowering agents,
ii) about 20 mg simvastatin as a lipid-regulating agent,
iii) about 0.8 mg folic acid as a serum homocysteine lowering agent;
wherein each specified dose is the daily dose.

\* \* \* \* \*